US009488613B2

(12) United States Patent
Bosch et al.

(10) Patent No.: US 9,488,613 B2
(45) Date of Patent: Nov. 8, 2016

(54) SYSTEMS, DEVICES AND METHODS FOR MULTIPLEXED DIAGNOSTICS

(71) Applicant: Massachusetts Institute of Technology, Cambridge, MA (US)

(72) Inventors: Irene Bosch, Brookline, MA (US); Kimberly S. Hamad-Schifferli, Somerville, MA (US); Lee Gehrke, Cotuit, MA (US); Nevan Clancy Hanumara, Kingston, RI (US); Jacqueline Linnes, West Lafayette, IN (US); David Wood, Somerville, MA (US); Jose F. Gomez-Marquez, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 110 days.

(21) Appl. No.: 14/014,864

(22) Filed: Aug. 30, 2013

(65) Prior Publication Data
US 2014/0246334 A1 Sep. 4, 2014

Related U.S. Application Data

(63) Continuation of application No. PCT/US2012/027613, filed on Mar. 2, 2012.

(60) Provisional application No. 61/448,614, filed on Mar. 2, 2011, provisional application No. 61/593,748, filed on Feb. 1, 2012.

(51) Int. Cl.
*G01N 27/26* (2006.01)
*G01N 21/01* (2006.01)
(Continued)

(52) U.S. Cl.
CPC ..... *G01N 27/3275* (2013.01); *B01L 3/502715* (2013.01); *G06K 7/015* (2013.01);
(Continued)

(58) Field of Classification Search
None
See application file for complete search history.

(56) References Cited

U.S. PATENT DOCUMENTS

| 4,056,359 | A | 11/1977 | Janin | |
|---|---|---|---|---|
| 2002/0090649 | A1* | 7/2002 | Chan et al. | 435/7.1 |

(Continued)

OTHER PUBLICATIONS

International Preliminary Report on Patentability by the International Bureau of WIPO for International Application No. PCT/US2012/027613 dated Sep. 3, 2013. (9 pages).
(Continued)

*Primary Examiner* — Jill Warden
*Assistant Examiner* — Timothy G Kingan
(74) *Attorney, Agent, or Firm* — McCarter & English, LLP; David R. Burns

(57) ABSTRACT

Exemplary embodiments provide diagnostic devices, systems and methods for determining the presence or absence of one or more markers or characteristics in one or more samples. An exemplary diagnostic device may display a first two-dimensional machine-readable output to indicate the presence or absence of a first characteristic in a sample. Similarly, the exemplary diagnostic device may display a second two-dimensional machine-readable output to indicate the presence or absence of a second characteristic in a sample. An image capture device may be used to automatically detect the two-dimensional machine-readable output appearing in the diagnostic device. A computational device may be used to automatically determine whether the presence or absence of the first characteristic and/or the second characteristic based on the two-dimensional machine-readable output displayed in the diagnostic device.

32 Claims, 15 Drawing Sheets

(51) Int. Cl.
- G01N 27/327 (2006.01)
- G06K 7/015 (2006.01)
- G06K 9/00 (2006.01)
- G06K 7/10 (2006.01)
- B01L 3/00 (2006.01)

(52) U.S. Cl.
CPC .......... *G06K 7/10* (2013.01); *G06K 9/00496* (2013.01); *B01L 2300/021* (2013.01); *B01L 2300/025* (2013.01); *B01L 2300/126* (2013.01); *B01L 2400/0406* (2013.01)

(56) References Cited

U.S. PATENT DOCUMENTS

| | | | |
|---|---|---|---|
| 2004/0087033 A1* | 5/2004 | Schembri | 436/180 |
| 2004/0248167 A1 | 12/2004 | Quake et al. | |
| 2005/0106713 A1* | 5/2005 | Phan et al. | 435/287.2 |
| 2010/0111764 A1 | 5/2010 | Groll | |
| 2010/0144020 A1 | 6/2010 | Kim et al. | |
| 2011/0017826 A1 | 1/2011 | Mohan et al. | |
| 2011/0195872 A1* | 8/2011 | Selinfreund et al. | 506/39 |
| 2013/0322595 A1* | 12/2013 | Connors | 378/48 |

OTHER PUBLICATIONS

International Search Report and Written Opinion by the International Searching Authority for International Application No. PCT/US2012/027613 dated Jun. 28, 2012. (11 pages).

Hasenbank, Melissa S., et al. "Demonstration of multi-analyte patterning using piezoelectric inkjet printing of multiple layers." Analytica chimica acta 611(1): 80-88 (Feb. 2, 2008).

Martinez, Andres W, et al. "Diagnostics for the developing world: microfluidic paper-based analytical devices." Analytical Chemistry 82.1 (Dec. 9, 2009): 3-10.

Martinez, Andres W., Scott T. Phillips, and George M. Whitesides. "Three-dimensional microfluidic devices fabricated in layered paper and tape." Proceedings of the National Academy of Sciences 105.50 (Oct. 29, 2008): 19606-19611.

New England Healthcare Institute. "Thinking Outside the Pillbox: A System-wide Approach to Improving Patient Medication Adherence for Chronic Disease" (Aug. 2009). Accessed on the Internet at http://www.nehi.net/writable/publication_files/file/pa_issue_brief_final.pdf on Mar. 19, 2015.

Osorio, Lyda, et al. "Comparison of the diagnostic accuracy of commercial NS1-based diagnostic tests for early dengue infection." Virol J, 7:361, (Dec. 6, 2010).

* cited by examiner

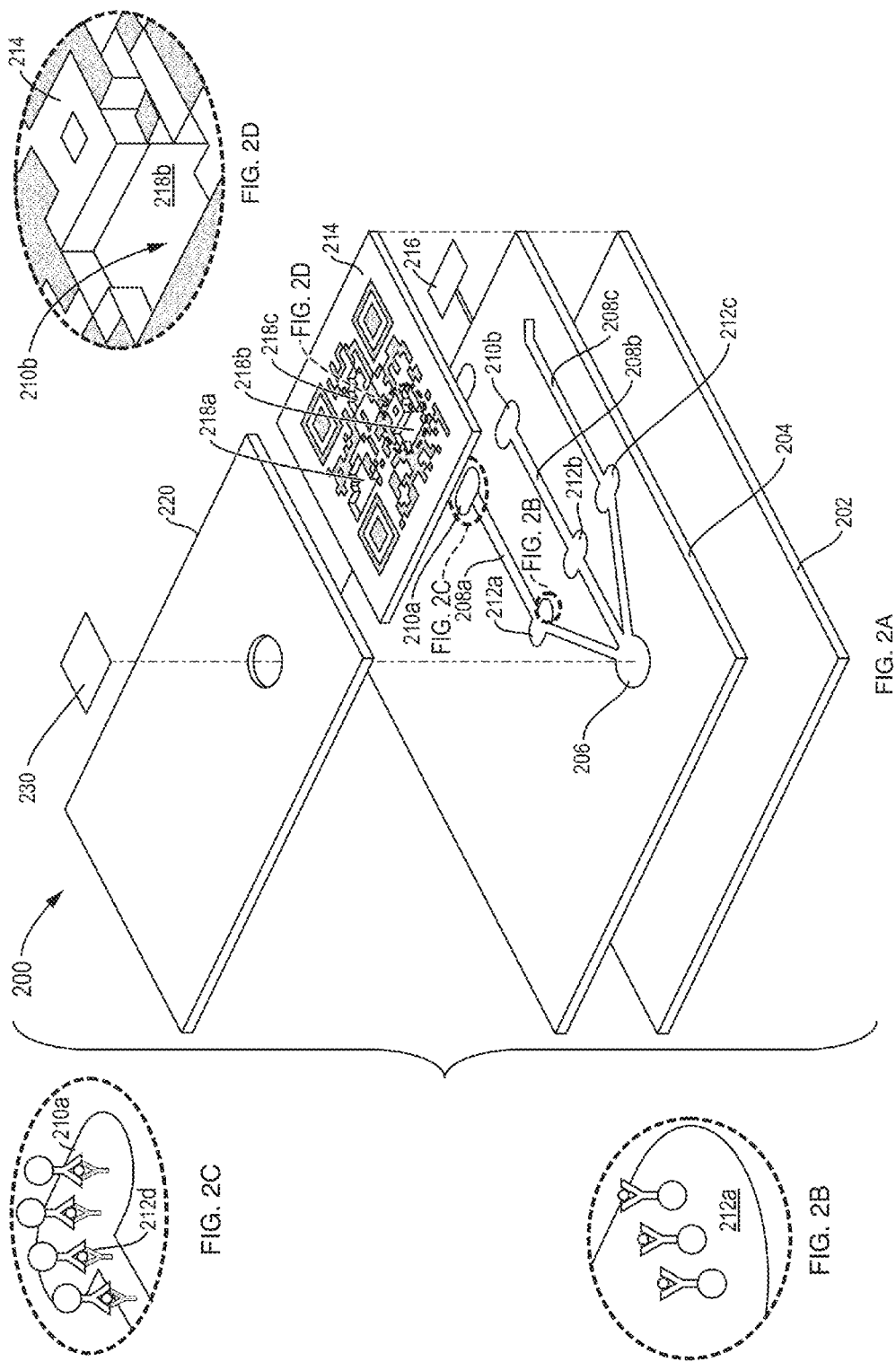

SYSTEMS, DEVICES AND METHODS FOR MULTIPLEXED DIAGNOSTICS

RELATED APPLICATIONS

The present application is a continuation application of International Application No. PCT/US2012/027613, filed Mar. 2, 2012, which claims priority to U.S. Provisional Patent Application No. 61/448,614, filed Mar. 2, 2011, and U.S. Provisional Patent Application No. 61/593,748, filed Feb. 1, 2012. The entire contents of each of the aforementioned applications are incorporated herein in their entirety by reference.

BACKGROUND

Microfluidic diagnostic devices are important in detecting biological and chemical markers in samples by analyzing the interactions of the markers with one or more reagents. FIG. 1A illustrates a perspective view of an exemplary conventional diagnostic strip 100 that is capable of detecting a biological or chemical marker in a sample. The diagnostic strip 100 includes an input node 102 that may be used to introduce a sample 104 to the strip 100. FIG. 1B illustrates a close-up view of the sample 104 introduced at the input node 102. The input node 102 is in fluid communication with a microfluidic channel 106 that includes a first reagent 108 that interacts with a marker in the sample. FIG. 1C illustrates a close-up view of the first reagent 108 provided at the microfluidic channel 106. The microfluidic channel 106 ends in a terminal output node 110 that includes a second reagent that interacts with the marker in the sample to display a first indicator line 112, and a third reagent that interacts with the marker to display a second indicator line 114. The result of the analysis of the sample is the display of the first indicator line 112 and/or the second indicator line 114 that may form a one-dimensional pattern that is read and interpreted by a human user.

SUMMARY

In accordance with an exemplary embodiment, a diagnostic device is provided for detecting a presence or absence of one or more substances in one or more samples. The diagnostic device includes a microfluidic network layer. The microfluidic network layer includes a first set of input nodes for introduction of the one or more samples to the diagnostic device and an output region. The output region includes a first set of output nodes arranged to detect the presence or absence of a first substance in the one or more samples, a second set of output nodes arranged to detect the presence or absence of a second substance in the one or more samples, and a two-dimensional machine-readable pattern overlaid over the first set of output nodes and the second set of output nodes to provide a machine-readable output indicating the presence or absence of the first or second substance in the one or more samples. The microfluidic network layer also includes a plurality of microfluidic channels extending between the first set of input nodes and the first and second sets of output nodes.

In accordance with another exemplary embodiment, a method is provided for detecting a presence or absence of one or more substances in one or more samples. The method includes introducing the one or more samples at a first set of input nodes of a diagnostic device, the introduction of the one or more samples resulting in a machine-readable output. The machine-readable output includes a first set of output nodes arranged to detect the presence or absence of a first substance in the one or more samples and a second set of output nodes arranged to detect the presence or absence of a second substance in the one or more samples. In an exemplary embodiment, the method includes using an image capture device to detect the machine-readable output, and using a computational device to automatically determine the presence of the first substance in the one or more samples based on the display of a first indicator at the first set of output nodes within the machine-readable output.

In accordance with another exemplary embodiment, a method is provided for forming a diagnostic device for detecting a presence or absence of one or more substances in one or more samples. The method includes providing a microfluidic network layer, forming a set of input nodes in the microfluidic network layer, and forming an output region. The output region includes a first set of output nodes arranged to detect the presence or absence of a first substance in the one or more samples, a second set of output nodes arranged to detect the presence or absence of a second substance in the one or more samples, and a two-dimensional machine-readable pattern overlaid over the first set of output nodes and the second set of output nodes to provide a machine-readable output indicating the presence or absence of the first or second substance in the one or more samples. The method also includes forming a plurality of microfluidic channels extending between the first set of input nodes and the first and second sets of output nodes.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 2A illustrates an exploded perspective view of an exemplary diagnostic device showing a network of microfluidic channels.

FIG. 2B is a close-up view of an exemplary reagent provided at a channel in the exemplary diagnostic device of FIG. 2A.

FIG. 2C is a close-view of an exemplary reagent provided at an output node in the exemplary diagnostic device of FIG. 2A.

FIG. 2D is a close-up view of an aperture in an exemplary stencil aligned over an output node in the exemplary diagnostic device of FIG. 2A.

DETAILED DESCRIPTION

Figure 1B:
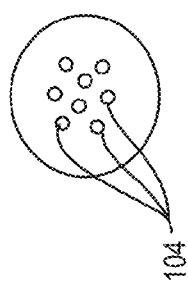
FIG. 1B (prior art) illustrates a close-up view of a sample introduced at an input node of the conventional diagnostic strip of FIG. 1A.
Figure 1C:
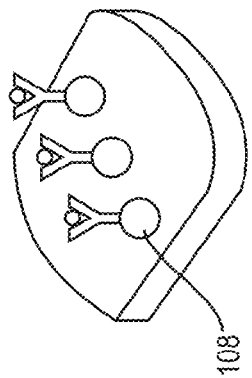
FIG. 1C (prior art) illustrates a close-up view of a reagent provided at a microfluidic channel of the conventional diagnostic strip of FIG. 1A.
Figure 1A:
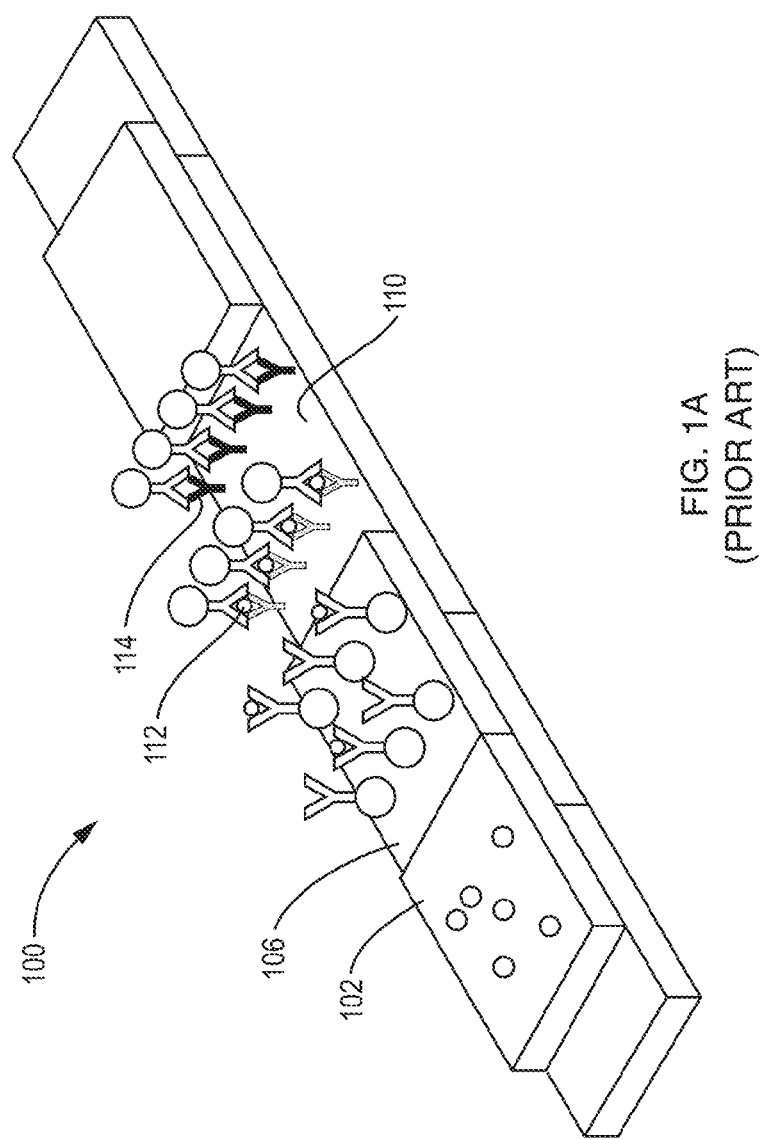
FIG. 1A (prior art) illustrates a perspective view of an exemplary conventional diagnostic strip.

Exemplary embodiments provide diagnostic devices, systems and methods for detecting the presence or absence of one or more markers or characteristics in one or more samples. An exemplary diagnostic device may display a machine-readable two-dimensional pattern to indicate, qualitatively and/or quantitatively, the presence or absence of one or more markers or characteristics in one or more samples. For example, a first machine-readable pattern may be displayed at an output region to indicate that a first marker is present in a sample, while a second machine-readable pattern may be displayed at the output region to indicate that the first marker is not present in the sample. An image capture device may be used to automatically detect the machine-readable pattern, and a computational device may be used to automatically determine whether the first marker is present or absent in the sample based on the machine-readable pattern displayed in the diagnostic device.

Exemplary markers or characteristics that may tested in an exemplary diagnostic device include, but are not limited to, the presence or absence of one or more physiological or disease conditions, one or more biological or chemical components (such as, proteins, nucleic acids, sugars), food, water, soil components, drugs, drug metabolites, biomarkers, tracers, biological organisms (such as, viruses, bacteria), one or more environmental factors (such as, pH), one or more controlled substances (such as, narcotics), and the like. Exemplary samples that may be tested include, but are not limited to, blood, blister exudate, sputum, urine, feces, soil, water, food, and the like.

Multiple exemplary diagnostic devices distributed to multiple users may enable broad and real-time surveillance of diseases and pathogens and their early detection. This allows for rapid crowdsourcing of detection results that may allow epidemiological examination and detection of pathogens and disease conditions spread over a population and/or a geographical region. This also enables rapid point-of-care detection of pathogens that threaten supplies of food, water and blood, and early localization of infected areas.

I. DEFINITION OF EXEMPLARY TERMS

Certain terms are defined in this section to facilitate understanding of exemplary embodiments.

The terms "diagnostic device" and "diagnostic system," as used herein, refer to a device or system that enables testing of one or more markers or characteristics in one or more samples.

The term "sample," as used herein, refers to a substance that may be tested for a marker or characteristic using an exemplary diagnostic device. Exemplary samples may include, but are not limited to, blood, blister exudate, sputum, urine, feces, soil, water, food, and the like.

The term "marker," as used herein, refers to a substance in a sample that may be used as an indicator of a biological or chemical state of the sample. Detection of a marker in a sample may indicate that the sample has a corresponding biological state. Exemplary biological states may include, but are not limited to, normal biological states (e.g., certain concentrations of sugar in a blood sample), pathogenic states (e.g., a virus in a tissue sample, a bacterium in a soil sample), pharmacologic states or responses (e.g., drug metabolites in a blood sample), and the like. Certain exemplary markers may include, but are not limited to, proteins, nucleic acids, sugars, food, water, soil components, drugs, drug metabolites, biomarkers, tracers, biological organisms like viruses, bacteria, one or more environmental factors (e.g., pH), one or more controlled substances (e.g., narcotics), one or more chemical compounds (e.g., oils, fuels, chemical additives), and the like.

The term "reagent," as used herein, refers to a substance that interacts with marker or characteristic of a sample. Interaction of a reagent with a marker or characteristic of a sample may cause the appearance or disappearance of an indicator in a diagnostic device. Exemplary interactions may include, but are not limited to, colorimetric interactions, electrochemical reactions, and the like. Exemplary reagents may include, but are not limited to, any suitable biological or chemical agent (e.g., antibodies, aptamers); nanoparticles, nanomaterials, nanocrystals, colloids, microspheres, microparticles; any suitable biological or chemical agent bound or tethered to one or more nanoparticles, nanomaterials, nanocrystals, colloids, microspheres, microparticles; and the like. Interaction of a sample with a reagent bound to an exemplary nanoparticle, nanomaterial, nanocrystal, colloid, microsphere or microparticle may enhance the expression of a color that may appear due to the interaction between the sample and the reagent.

Exemplary nanoparticles, nanomaterials, nanocrystals, colloids, microspheres and microparticles may include metals, for example, gold (enhancing a red color when a marker binds with it), silver (enhancing a green and/or blue color when a marker binds with it), copper (enhancing one or more colors ranging from red to green when a marker binds with it), and the like. Exemplary nanoparticles, nanomaterials, nanocrystals, colloids, microspheres and microparticles may include oxides, for example, iron oxide (enhancing a brown color when a marker binds with it). Exemplary nanoparticles, nanomaterials, nanocrystals, colloids, microspheres and microparticles may include semiconductor materials that may enhance one or more colors spanning the entire visible spectrum, for example, cadmium selenide (CdSe), cadmium sulfide (CdS), indium arsenide (InAs), indium phosphide (InP), and the like. Exemplary nanoparticles, nanomaterials, nanocrystals, colloids, microspheres and microparticles may be carbon-based and may enhance a black appearance, for example, carbon nanotubes, graphene, fullerenes, and the like.

The term "machine-readable pattern," as used herein, refers to a visible pattern that encodes data according to a predefined specification. In an exemplary diagnostic device, an incomplete machine-readable pattern may be provided along with one or more output nodes at an output region. The presence or absence of visual indicators at the output nodes may result in the formation of one or more completed machine-readable patterns. For example, if a single output node is provided in an incomplete machine-readable pattern, appearance of a visual indicator at the output node may result in a first pattern, while lack of a visual indicator at the output node may result in a second pattern. Exemplary diagnostic devices may thereby allow distinguishing between different diagnostic results obtained at the output nodes of the exemplary diagnostic device based on different visible patterns. Exemplary embodiments may provide and/or store a mapping between different machine-readable patterns and their corresponding diagnostic results to allow interpretation of the patterns.

In an exemplary embodiment, a machine-readable pattern may encode data that is independent of the content of the pattern. The machine-readable pattern may thereby provide encryption of the diagnostic results obtained at the output nodes of an exemplary diagnostic device. For example, the machine-readable pattern may prevent the user from interpreting the diagnostic results simply by viewing the pattern. This also allows decoupling of the interpretation of the pattern (for example, automatically at a computational device) from the use of the diagnostic device. This avoids human mistakes in interpreting whether a sample has a marker or characteristic based on the visible pattern. The decoupling also avoids causing the user stress or anxiety about the diagnostic results and prevents a user from corrupting the results or providing incorrect results.

Exemplary machine-readable patterns may be one-dimensional (e.g., a barcode), two-dimensional (e.g., a Quick Response code, a customized Quick Response code, a matrix), three-dimensional (e.g., an encoded hologram), and the like.

The term "patient," as used herein, refers to any type of animal, human or non-human, from whom a biological sample may be derived for testing using an exemplary diagnostic device.

II. FIRST NON-LIMITING EXEMPLARY DIAGNOSTIC DEVICE

FIGS. 2A-2E illustrate an exemplary diagnostic device 200 that displays a machine-readable two-dimensional pattern to qualitatively and/or quantitatively indicate the presence or absence of one or more markers or characteristics in one or more samples. For example, a first machine-readable pattern may be displayed at an output region to indicate that a first marker is present in a sample, while a second machine-readable pattern may be displayed at the output region to indicate that the first marker is not present in the sample. In some exemplary embodiments, a single two-dimensional pattern may be generated as a result of analyzing one or more samples in an exemplary diagnostic device. In some other exemplary embodiments, two or more two-dimensional patterns may be generated as a result of analyzing one or more samples in an exemplary diagnostic device.

A visible two-dimensional pattern generated at an output region of the diagnostic device 200 may be read manually or detected automatically by a machine, e.g., a barcode reader, a computing or communication device equipped with image capture technology, and the like. An image or identification of the visible two-dimensional pattern may be automatically transmitted by a computing or communication device. Allowing machine reading of a machine-readable two-dimensional pattern generated by an exemplary diagnostic device is advantageous over conventional test strips that rely on human involvement in reading and/or transmitting of diagnostic results. For example, a color-blind user may be unable to detect the appearance of certain colors in a conventional test strip. Similarly, appearance of alphanumeric codes in a conventional test strip may pose a problem for illiterate users. Exemplary diagnostic devices address these deficiencies in conventional test strips by eliminating the reliance on a human user to read the diagnostic results and to transmit them.

In addition, allowing machine reading of a machine-readable two-dimensional pattern generated by an exemplary diagnostic device is advantageous over conventional test strips that require or allow a human user to identify a diagnostic result. For example, a user of a conventional pregnancy test kit may require information on how the appearance of a control band and a test band corresponds to the diagnostic results. In addition, the user may need to use her subjective judgment on whether a test band is visible in the conventional pregnancy test kit. Addition, based on the user's interpretation of the diagnostic results, the user may decide whether to report and transmit the diagnostic results.

Exemplary diagnostic devices address these deficiencies in conventional test strips by generating two-dimensional machine-readable patterns that may encode diagnostic result data that are independent of the actual content of the patterns. The machine-readable pattern may thereby provide encryption of the diagnostic results obtained at the output nodes of an exemplary diagnostic device. For example, a user may not be able to or be required to interpret exemplary machine-readable patterns, thus eliminating subjective human error in determining diagnostic results. Furthermore, this avoids causing the user stress or anxiety about the diagnostic results and prevents a user from corrupting the results or deciding against reporting the results. Further, generation of a machine-readable pattern in an exemplary diagnostic device protects user privacy because the pattern prevents identification of the source of the sample (e.g., a patient from whom a sample was taken) merely based on an inspection of the machine-readable pattern.

In one example, the diagnostic device 200 of FIGS. 2A-2E may be used to detect a marker or characteristic of a single sample. In another example, the diagnostic device 200 of FIGS. 2A-2E may be used to simultaneously and rapidly detect a plurality of markers or characteristics in a single sample or a plurality of markers or characteristics in a plurality of samples. Exemplary device 200 may be used to detect markers or characteristics in any number of samples including, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and the like. Exemplary device 200 may be used to detect any number of markers or characteristics in one or more samples including, but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and the like.

The ability to concurrently detect and analyze multiple markers in a multiplexed manner in exemplary diagnostic device 200 enhances the accuracy of identifying an unknown secondary condition (e.g., the presence of a virus) in a sample. For example, the secreted non-structural protein 1 of a dengue virus (sNS1) and the IgG and IgM antibodies may be detected simultaneously in a sample by an exemplary diagnostic device to determine the presence of a dengue virus as well as the onset of the physiological response the dengue virus. A conventional non-multiplexed test strip is unlikely to achieve a high level of accuracy in determining a secondary condition based on multiplexed diagnostic results. This is because overlaying multiple detection conjugates and detection proteins could lead to false signals, cross-contamination and interference on a conventional test strip. In contrast, multiplexing achieved in exemplary diagnostic devices enhances the accuracy of identification of a secondary condition by performing multiplexed detection of multiple markers uniquely associated with the condition.

FIG. 2A illustrates an exploded perspective view of the exemplary diagnostic device 200 showing a network of microfluidic channels. The diagnostic device 200 may include a bottom layer 202 provided to support one or more layers disposed above it. The bottom layer may be impermeable to and may not conduct samples, thereby preventing leakage of the samples from the diagnostic device. In an exemplary embodiment, the bottom layer 202 may be formed of contact paper with the adhesive surface facing up or toward a network layer including one or more microfluidic channels.

The diagnostic device 200 may include a microfluidic network layer 204 disposed above and supported by the bottom layer 202. In an exemplary embodiment, the diagnostic device 200 may include a single microfluidic network layer. In other exemplary embodiments, the diagnostic device 200 may include two or more microfluidic network layers stacked vertically. The material layers may be formed of a paper-based or paper-type material in some exemplary embodiments, for example, paper, nitrocellulose, and the like. Exemplary paper-based network layer is described in Martinez A. W., Phillips S. T., Whitesides G. M., Carrilho E., "Diagnostics for the Developing World: Microfluidic Paper-Based Analytical Devices," *Anal. Chem.*, 2010, 82(1):3-10, the entire contents of which are incorporated herein in their entirety by reference.

The network layer 204 may include one or more input nodes 206 at which one or more samples may be introduced into the diagnostic device 200. In an exemplary embodiment including a plurality of input nodes 206, the input nodes may be organized in any suitable manner in the diagnostic device 200 including, but not limited to, linear, circular, oval, ring, wavy, rectangular, square, matrix, random, scattered, and the like. In an exemplary embodiment, an input node 206 may be associated with a suitable alphanumeric or pictorial indicator to direct a user to introduce a sample at the input node 206.

The network layer 204 may include one or more microfluidic channels 208a, 208b, 208c coupled to at least one of the input nodes 206 for providing a pathway for a sample to flow from at least one input node to one or more terminal output nodes (for example, exemplary output nodes 210a, 210b, 210c). For example, channel 208a may extend between input node 206 and output node 210a, and channel 208b may extend between input node 206 and output node 210b. The channels 208a, 208b, 208c may be substantially two-dimensional or three-dimensional. The channels 208a, 208b, 208c may have exemplary widths ranging from about a millimeter to several millimeters.

An exemplary input node may be in fluid communication with a single channel in the network layer 204. Another exemplary input node may be multiplexed and may be in fluid communication with a plurality of channels in the network layer 204. For example, the exemplary input node 206 in FIG. 2A is in fluid communication with three exemplary channels 208a, 208b, 208c. Another exemplary input node may not be in fluid communication with any output nodes. In exemplary embodiments, an input node may be in fluid communication with any suitable number of channels and output nodes including, but not limited to, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and the like.

In an exemplary embodiment, a plurality of samples may be introduced at a plurality of input nodes and may flow through different sets of channels. That is, the channels configured to conduct each sample may be separate and independent of the channels configured to conduct the other samples. In another exemplary embodiment, a first channel configured to conduct a first sample introduced at a first input node may interact with a second channel configured to conduct a second sample introduced at a second input node. Direct interaction between the two samples may be detected in one or more output nodes, for example, as colors, patterns (e.g., splotches), and the like, that are generated as a result of the interaction.

Different configurations and connections among the input nodes 206 and the output nodes 210a, 210b, 210c are possible in exemplary embodiments. For example, a single input node may be in fluid communication with a single output node, a single input node may be in fluid communication with a plurality of output nodes, a plurality of input nodes may be in fluid communication with a single output node, and an input node may not be in fluid communication of any output nodes, and the like. Any combinations of such configurations may be provided in the same network layer 204.

The provision of separate channels leading to different discrete output nodes in exemplary diagnostic device 200 allows for simultaneous and rapid detection of the presence or absence of a plurality of markers or characteristics in one or more samples. For example, a first sample (e.g., urine) may be introduced at a first input node, may interact with a first set of one or more reagents along a first channel, and may result in the appearance or lack of a visual indicator at a first output node. Simultaneous with the first sample, a second sample (e.g., blood) may be introduced at a second input node, may interact with a second set of one or more reagents along a second channel, and may result in the appearance or lack of a visual indicator at a second output node. Similarly, the first sample may be introduced at a third input node, may interact with a third set of one or more reagents along a third channel, and may result in the appearance or lack of a visual indicator at a third output node.

The network layer 204 may include one or more reagents that may or may not interact with a sample to indicate the presence or absence of one or more markers or characteristics in the sample. In exemplary embodiments, the one or more reagents may be provided at the input nodes 206, the channels 208a, 208b, 208c (for example, reagents 212a, 212b, 212c) and/or the output nodes 210a (for example, reagent 212d), 210b, 210c. The one or more reagents may be provided in the network layer 204 in any suitable way, for example, as embedded in the network layer 204, as coated on components of the network layer 204, as provided on pads attached to the network layer 204, as provided in wells formed in the network layer 204, and the like. FIG. 2B is a close-up view of an exemplary reagent 212a provided at a channel 208a. FIG. 2C is a close-view of an exemplary reagent 212d provided at an output node 210a.

Exemplary reagents may include, but are not limited to, any suitable biological or chemical agent (e.g., antibodies, aptamers); nanoparticles, nanomaterials, nanocrystals, colloids, microspheres, microparticles; any suitable biological or chemical agent bound or tethered to one or more nanoparticles, nanomaterials, nanocrystals, colloids, microspheres, microparticles; and the like. Interaction of a sample with a reagent bound to an exemplary nanoparticle, nanomaterial, nanocrystal, colloid, microsphere or microparticle may enhance the expression of a color that may appear due to the interaction between the sample and the reagent.

Exemplary nanoparticles, nanomaterials, nanocrystals, colloids, microspheres and microparticles may include metals, for example, gold (enhancing a red color when a marker binds with it), silver (enhancing a green and/or blue color when a marker binds with it), copper (enhancing one or more colors ranging from red to green when a marker binds with it), and the like. Exemplary nanoparticles, nanomaterials, nanocrystals, colloids, microspheres and microparticles may include oxides, for example, iron oxide (enhancing a brown color when a marker binds with it). Exemplary nanoparticles, nanomaterials, nanocrystals, colloids, microspheres and microparticles may include semiconductor materials that may enhance one or more colors spanning the entire visible spectrum, for example, cadmium selenide (CdSe), cadmium sulfide (CdS), indium arsenide (InAs), indium phosphide (InP), and the like. Exemplary nanoparticles, nanomaterials, nanocrystals, colloids, microspheres and microparticles may be carbon-based and may enhance a black appearance, for example, carbon nanotubes, graphene, fullerenes, and the like.

The interaction of a sample and one or more reagents may result in the appearance or lack of visible indicators at one or more output nodes. Any suitable visible indicator may appear at an output node of the diagnostic device. An exemplary visible indicator may be the appearance of a particular color at the output node that is different from the underlying color of the output node or the surrounding regions. For example, if the underlying color of the output node and the surrounding regions is white, then interaction of a sample with a reagent may result in the appearance of a pink color at the output node, indicating that the sample has a tested marker or characteristic. Another exemplary visible indicator may be the appearance of one or more alphanumeric characteristics at the output node. Another exemplary visible indicator may be the appearance of one or more pictorial symbols at the output node. Another exemplary visible indicator may be the combination of a color and one or more alphanumeric and/or pictorial symbols at the output node.

One of ordinary skill in the art will recognize that exemplary indicators appearing at an output region of a diagnostic device may be visual or non-visual. In an exemplary embodiment, the presence or absence of a marker in a sample may result in an electrochemical reaction or activity in the diagnostic device. For example, one or more output nodes in the diagnostic device associated with a marker may be electrochemically active if the marker is present in a sample, and may be electrochemically inactive if the marker is absent in the sample. An external reader may be used to detect the electrochemical activity of each output node in the matrix of diagnostic device. The electrochemical activity of the output nodes may be detected in sequence or in parallel by the reader. Exemplary electrochemical activity readers may include, but are not limited to, glucometers, multimeters, capacitive touch screens and other electrosensitive probes that operate at a point (e.g., to detect electrochemical activity at output nodes in sequence) or in a plane (e.g., to detect electrochemical activity at output nodes in parallel).

The appearance and/or absence of visible indicators at one or more output nodes may form or complete a two-dimensional machine-readable pattern at the output region of the device that is readable at 360 degrees (omni-directionally). The two-dimensional pattern may be interpreted to determine the presence or absence of one or more particular markers and/or characteristics in the sample. An exemplary two-dimensional machine-readable pattern may take the form of a Quick Response (QR) code, a customized QR code, a matrix pattern, and the like, but is not limited to these exemplary patterns.

In an exemplary embodiment, a first set of one or more reagents 212a, 212b, 212c may be provided along the channels 208a, 208b, 208c and a second set of one or more reagents may be provided at one or more output nodes 210a, 210b, 210c. The presence of a pathogen protein in a sample may be detected, for example, by providing a first anti-pathogen monoclonal antibody bound to gold nanoparticles 212a along a channel 208a, and a second anti-pathogen monoclonal antibody 212d at an output node 210a. The gold nanoparticles may enhance the expression of a red color that may appear at the output node 210a due to the interaction of the pathogen protein with the reagent 212a bound to the gold nanoparticles. If a pathogen protein is present in the sample, it binds initially to the first monoclonal antibody 212a bound to the gold nanoparticles and subsequently to the second monoclonal antibody 212d. These interactions result in the expression of a red color at the output node 210a.

In an exemplary embodiment, a two-dimensional machine-readable pattern may be printed or etched at the output region of the diagnostic device 200. The pattern may include one or more empty portions at which the output nodes 210a, 210b, 210c may be configured or provided. The display or non-display of visible indicators at the output nodes 210a, 210b, 210c may determine the final appearance of the pattern at the output region of the device 200.

In another exemplary embodiment, a separate layer or stencil 214 having a two-dimensional pattern printed on a surface may be provided over the network layer 204 at the output region of the layer 204 so that the printed surface of the stencil 214 faces the user. The stencil 214 may include one or more apertures 218a, 218b, 218c aligned along one or more output nodes 210a, 210b, 210c, respectively, so that the output nodes fall within the scope of the pattern on the stencil 214 and so that the output nodes are viewable by a user. The display or non-display of visible indicators at the output nodes 210a, 210b, 210c may determine the final appearance of the pattern at the output region of the device 200. FIG. 2D is a close-up view of an exemplary aperture 218b in the stencil 214 aligned over an output node 210b.

In an exemplary embodiment, one or more channels 208a, 208b, 208c may be selectively inserted into or removed from the network layer 204 before use and between uses. In an exemplary embodiment, one or more magnetic materials (e.g., magnetic ink) may be provided at a selected channel and an electric field may be applied to the network layer 204 to insert the selected channel into the network layer or to remove the selected channel from the network layer.

In an exemplary embodiment, the network layer 204 may be a paper-based microfluidic circuit formed of filter paper. The porosity of the filter paper may facilitate the flow of fluids by capillary action through the channels 208a, 208b, 208c in the network layer 204 without the use of or need for an external pumping mechanism. In other exemplary embodiments, the network layer 204 may incorporate both paper-fluidic components that rely on lateral flow of fluids and lab-on-chip components that do not rely on lateral flow of fluids. In an exemplary embodiment, one or more lab-on-chip components may be used at the input nodes 206, along the channels 208, and/or at the output nodes 210. In an exemplary embodiment, one or more wicks may be provided at the beginning of one or more channels to facilitate flow of a sample into the channels via capillary action.

In an exemplary embodiment, one or more absorbent pads 216 may be provided at one or more output nodes to direct a sample to the output nodes and to prevent leakage of the sample out of the output nodes. An exemplary absorbent pad may maintain the motive force acting on the sample in the network layer 204 by absorbing fluid from the directional wicking channels 208a, 208b, 208c after the sample passes the output nodes. In an exemplary embodiment, the absorbent pad 216 may be formed of a paper material.

In an exemplary embodiment, the diagnostic device 200 may include a top layer 220 to cover the channels in the network layer 204 to prevent contamination and viewing or tampering of the fluid flow through the network layer 204. In an exemplary embodiment, the top layer 220 may include one or more apertures for accessing the input nodes. The apertures for the input nodes may be covered by removable covers or tabs, for example, tab 230, that may be selectively removed to access one or more input nodes. This provides a switching or valving mechanism by which a user may selectively make connections in the diagnostic device.

In an exemplary embodiment, a user may punch out certain input nodes and/or channels to select activation points in an inverse fashion by blocking access to the punched-out input nodes and/or channels. One or more removable tabs may be provided in the input nodes and/or channels to enable the user to remove material from the input nodes and/or the channels. For example, removal of a tab may result in the removal of material from a corresponding input node or channel, thereby breaking the connection between the input node and an output node. This provides a switching or valving mechanism by which a user may selectively break connections in the diagnostic device.

In an exemplary embodiment, the top layer 220 may include one or more apertures or transparent windows for viewing the output nodes. In an exemplary embodiment, the top layer 220 may be formed of contact paper with the adhesive surface facing toward the bottom layer 202. The top layer 220 and the bottom layer 202 may be attached to each other to sandwich the network layer 204 in between.

Figure 2E:
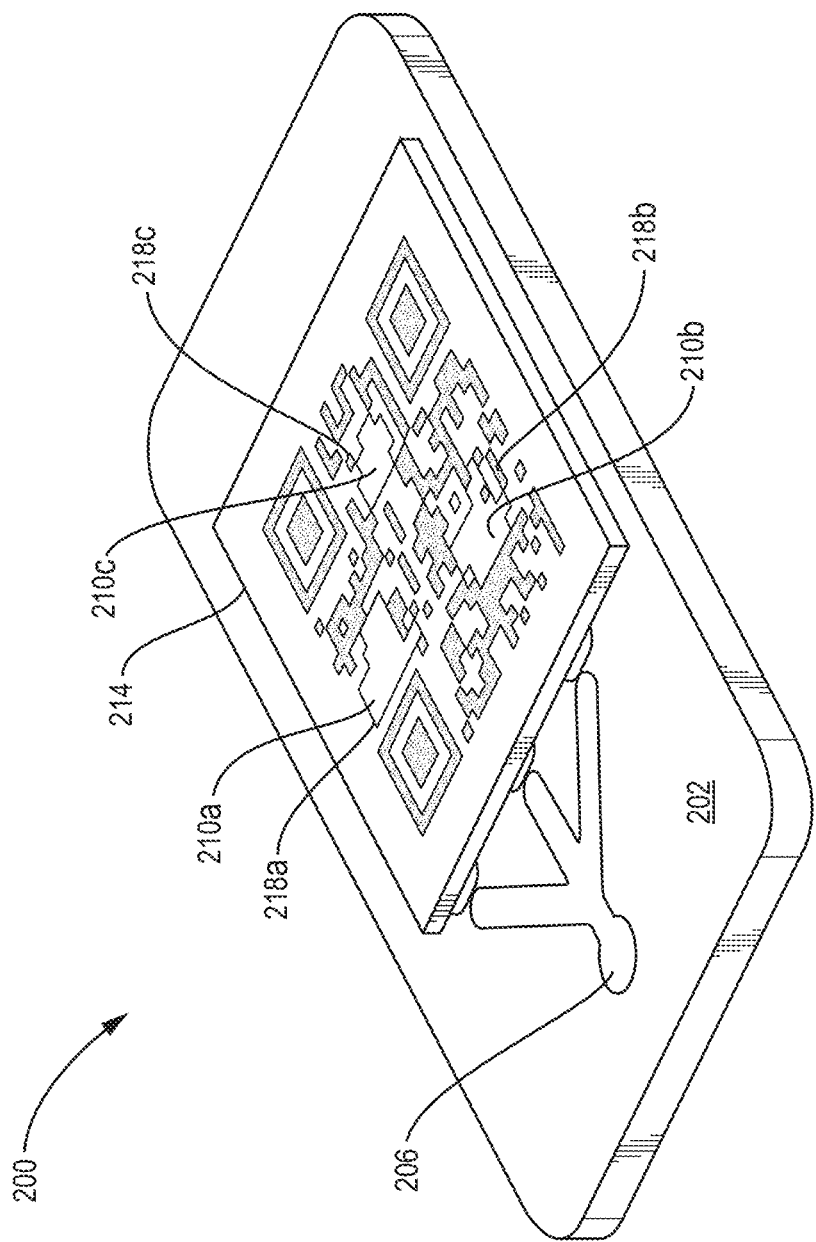
FIG. 2E illustrates a perspective view of the exemplary diagnostic device of FIG. 2A in an assembled state.

FIG. 2E illustrates a perspective view of the exemplary diagnostic device 200 of FIG. 2A in an assembled state. The stencil 214 has a machine-readable two-dimensional pattern printed on a surface facing the user. The stencil 214 may include three exemplary apertures 218a, 218b, 218c provided integrally with the printed pattern to reveal three corresponding output nodes 210a, 210b, 210c, respectively, in the network layer 204 underlying the stencil 214. This allows the presence or absence of visible indicators at the output nodes 210a, 210b, 210c to determine the appearance of the overall two-dimensional pattern in the matrix stencil 214.

Figure 3:
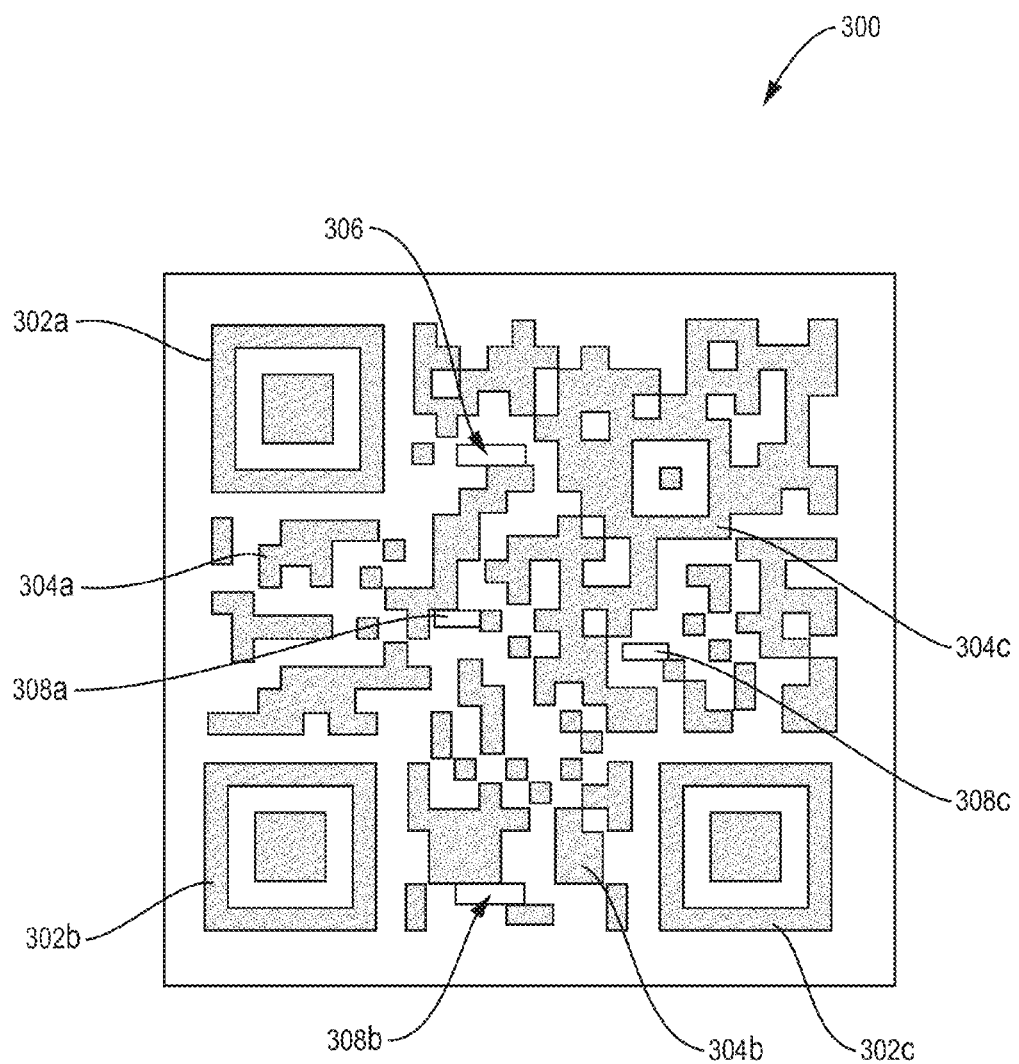
FIG. 3 illustrates a top view of an exemplary two-dimensional machine-readable pattern that may appear at an output region of an exemplary diagnostic device.

FIG. 3 illustrates a top view of an exemplary two-dimensional machine-readable pattern 300 that may be provided at the output region of an exemplary diagnostic device. The exemplary two-dimensional pattern 300 is a Quick Response (QR) code, but other patterns are possible. The exemplary pattern 300 may include one or more position detection patterns 302a, 302b, 302c at the corners of the pattern 300 to enable automatic detection of the position of the pattern, which allows detection and interpretation of the pattern at 360 degrees, i.e., omnidirectionally. The exemplary pattern 300 may include one or more pre-printed portions (e.g., portions 304a, 304b, 304c) that are always displayed regardless of the diagnostic results generated by the device. The exemplary pattern 300 may include one or more pre-printed background portions 306 that always display a background color that is different from a color that is displayed to indicate the presence of a marker or characteristic in a sample.

In an exemplary embodiment, the exemplary two-dimensional machine-readable pattern 300 may be directly printed or etched on a surface of the microfluidic network layer of the diagnostic device. In another exemplary embodiment, the exemplary two-dimensional machine-readable pattern 300 may be provided on a separate layer or stencil than the microfluidic network layer. The separate layer or stencil may be disposed above the microfluidic network layer in the diagnostic device.

The exemplary pattern 300 may include one or more test portions (e.g., portions 308a, 308b, 308c) at which one or more visible indicators may appear based on the interaction of one or more sample with one or more reagents provided in the diagnostic device. In an exemplary embodiment in which the pattern 300 is printed or etched on a surface of the microfluidic network layer, the test portions 308a, 308b, 308c may be empty portions at which output nodes may be configured. In another exemplary embodiment in which the pattern 300 is provided on a separate layer or stencil, the test portions 308a, 308b, 308c may be apertures aligned along the output nodes of the microfluidic network layer. This alignment allows a user to view visible indicators appearing at the output nodes within the scope of the pattern 300.

As such, upon use of the diagnostic device, the interaction or the lack of interaction of a sample with one or more reagents may result in a particular appearance of the overall two-dimensional pattern, where the overall pattern varies based on the presence or absence of a visible indicator at each output node. The mappings between different two-dimensional patterns and their corresponding diagnostic results may be stored on a storage device or in a database, and may be looked up by a user or a computing device.

In one example, the presence of a first marker in a sample may cause a visible indicator to appear only in test portion 308a. Thus, the presence of the first marker in a sample may be indicated by a first two-dimensional pattern in which a visible indicator appears in test portion 308a but in which visible indicators do not appear in test portions 308b and 308c. In another example, the presence of a second marker in a sample may cause a visible indicator to appear in test portions 308b and 308c. Thus, the presence of the second marker in a sample may be indicated by a second two-dimensional pattern in which a visible indicator does not appear in test portion 308a but in which visible indicators appear in test portions 308b and 308c. In another example, the presence of both the first and second markers in a sample may be indicated by a third two-dimensional pattern in which visible indicators appear in test portions 308a, 308b, 308c. One of ordinary skill will recognize that other configurations are possible for detection of one or more markers or characteristic in one or more samples.

In an exemplary embodiment, the intensity of a visible indicator at one or more output nodes may vary based on the extent of the interaction between a marker in a sample and one or more reagents. In an exemplary embodiment, an intensity of the visible indicator corresponding to a marker in a sample may increase or decrease in proportion to one or more aspects of the marker, for example, quantity, volume, concentration, strength, an extent or level of interaction of the marker with one or more reagents provided in the device, and the like. This allows quantitative analyses to be performed regarding the marker in the sample by analyzing the intensity of the visible indicator. In an exemplary embodiment, a quantitative determination of a marker in a sample may be performed based on a comparison between the intensity of a visible indicator at a test portion 308a, 308b, 308c and the background portion 306. Since the background portion 306 indicates a baseline color that indicates lack of a marker in a sample, a difference between an intensity of a visible indicator at a test portion and the intensity of the baseline color at the background portion may be proportionate to the quantitative level (or amount, volume, concentration or strength) of the marker in the sample. In an exemplary embodiment, the quantitative determination of a marker in a sample may then be used to make a secondary determination, for example, a physiological or disease condition.

In an exemplary embodiment, one or more positive control portions and/or one or more negative control portions may also be provided in the exemplary two-dimensional pattern 300. The positive control portions may be configured to always display visual indicators and the negative control portions may be configured to always lack visual indicators, regardless of the sample introduced in the diagnostic device. Providing the positive and negative control portions allows testing of the diagnostic device to ensure that the device has been assembled correctly. For example, if a positive control portion lacks a visual indicator and/or if a negative control portion displays a visual indicator, this may indicate that the diagnostic device is faulty and needs to be repaired or discarded.

Figure 4:
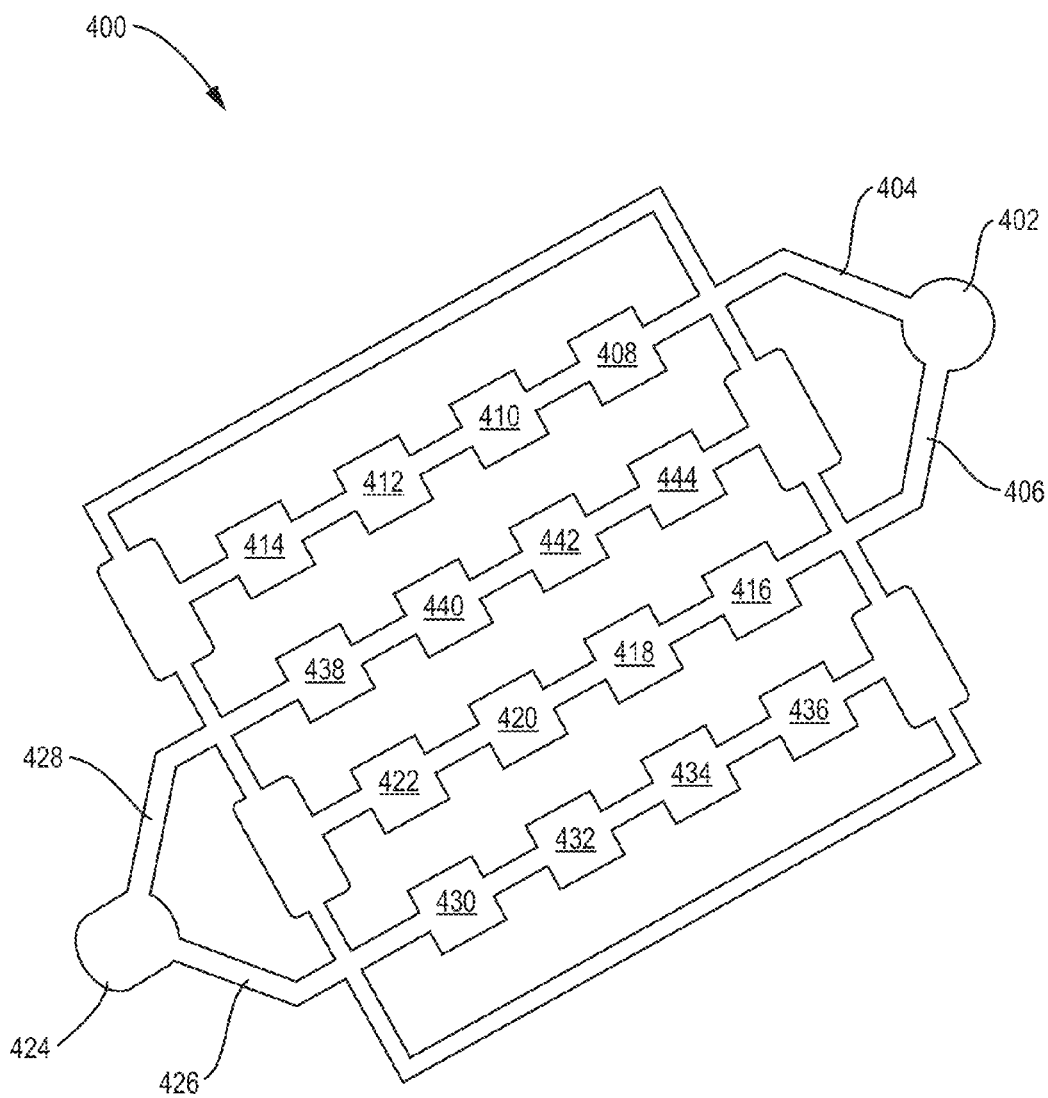
FIG. 4 illustrates a top view of an exemplary network layer of a diagnostic device.

FIG. 4 illustrates a top view of an exemplary network layer 400 of a diagnostic device including an output region configured as a two-dimensional matrix. Visible indicators appearing at one or more output nodes in the matrix may form an overall two-dimensional machine-readable pattern without the need or use of a stencil. Exemplary network layer 400 may include a first input node 402 that is multiplexed to be coupled to two channels 404, 406 that may be provided with one or more reagents. Channel 404 may include four exemplary output nodes 408, 410, 412, 414. Channel 406 may include four exemplary output nodes 416, 418, 420, 422. The exemplary network layer 400 may include a second input node 424 that is multiplexed to be coupled to two channels 426, 428 that may be provided with one or more reagents. Channel 426 may include four exemplary output nodes 430, 432, 434, 436. Channel 428 may include four exemplary output nodes 438, 440, 442, 444. Together, the output nodes 408, 410, 412, 414, 416, 418, 420, 422, 430, 432, 434, 438, 440, 442 and 444 may create a two-dimensional matrix pattern having an exemplary 4×4 configuration. One or more visual indicators may appear at one or more output nodes in the matrix pattern during testing of a sample.

In an exemplary embodiment, one or more of the output nodes in the matrix may form background portions. A background portion may always display a background color that is different from a color that is displayed at an output node to indicate the presence of a marker or characteristic in a sample. In an exemplary embodiment, a quantitative determination of the level (or amount, volume, concentration or strength) of a marker in a sample may be performed based on a comparison between the intensity of the visual indicator appearing at a test output node and a background portion. Since the background portion indicates a baseline color that indicates lack of a marker or characteristic, a difference between an intensity of a color at a test output node and the intensity of the baseline color at the background portion may be proportionate to the quantitative level of the marker or characteristic in the sample. In an exemplary embodiment, the quantitative determination of a marker or characteristic in a sample may then be used to make a secondary determination, for example, a physiological or disease condition.

In an exemplary embodiment, one or more of the output nodes in the matrix may form control portions. In an exemplary embodiment, one or more positive control portions and/or one or more negative control portions may be provided on an exemplary two-dimensional pattern. The positive control portions may be configured to always display visual indicators and the negative control portions may be configured to always lack visual indicators, regardless of the sample introduced in the device. Providing the positive and negative control portions allows testing of the diagnostic device to ensure that the device has been assembled correctly. For example, if a positive control portion lacks a visual indicator and/or if a negative control portion displays a visual indicator, this may indicate that the diagnostic device is faulty and needs to be repaired or discarded.

In an exemplary embodiment, the presence or absence of a marker in a sample may result in an electrochemical reaction or activity in the diagnostic device 400. For example, one or more output nodes in the diagnostic device associated with a marker may be electrochemically active if the marker is present in a sample, and may be electrochemically inactive if the marker is absent in the sample. An external reader may be used to detect the electrochemical activity of each output node in the matrix of diagnostic device 400. The electrochemical activity of the output nodes may be detected in sequence or in parallel by the reader. Exemplary electrochemical activity readers may include, but are not limited to, glucometers, multimeters, capacitive touch screens and other electrosensitive probes that operate at a point (e.g., to detect electrochemical activity at output nodes in sequence) or in a plane (e.g., to detect electrochemical activity at output nodes in parallel).

One of ordinary skill in the art will recognize that matrices of other dimensions are possible in exemplary diagnostic device. For example, one-dimensional matrices may include a linear arrangement of 2, 3, 4, 5, 6, 7, 8, 9, 10, 11, 12, 13, 14, 15, 16, 17, 18, 19, etc., output nodes. Other two-dimensional matrices may include 2×2, 2×3, 3×3, 3×4, 4×2, 4×5, 5×3, 5×2, 5×5 matrices, and the like. Three-dimensional matrices are also possible, for example, a 4×4×4 matrix.

Figure 5:
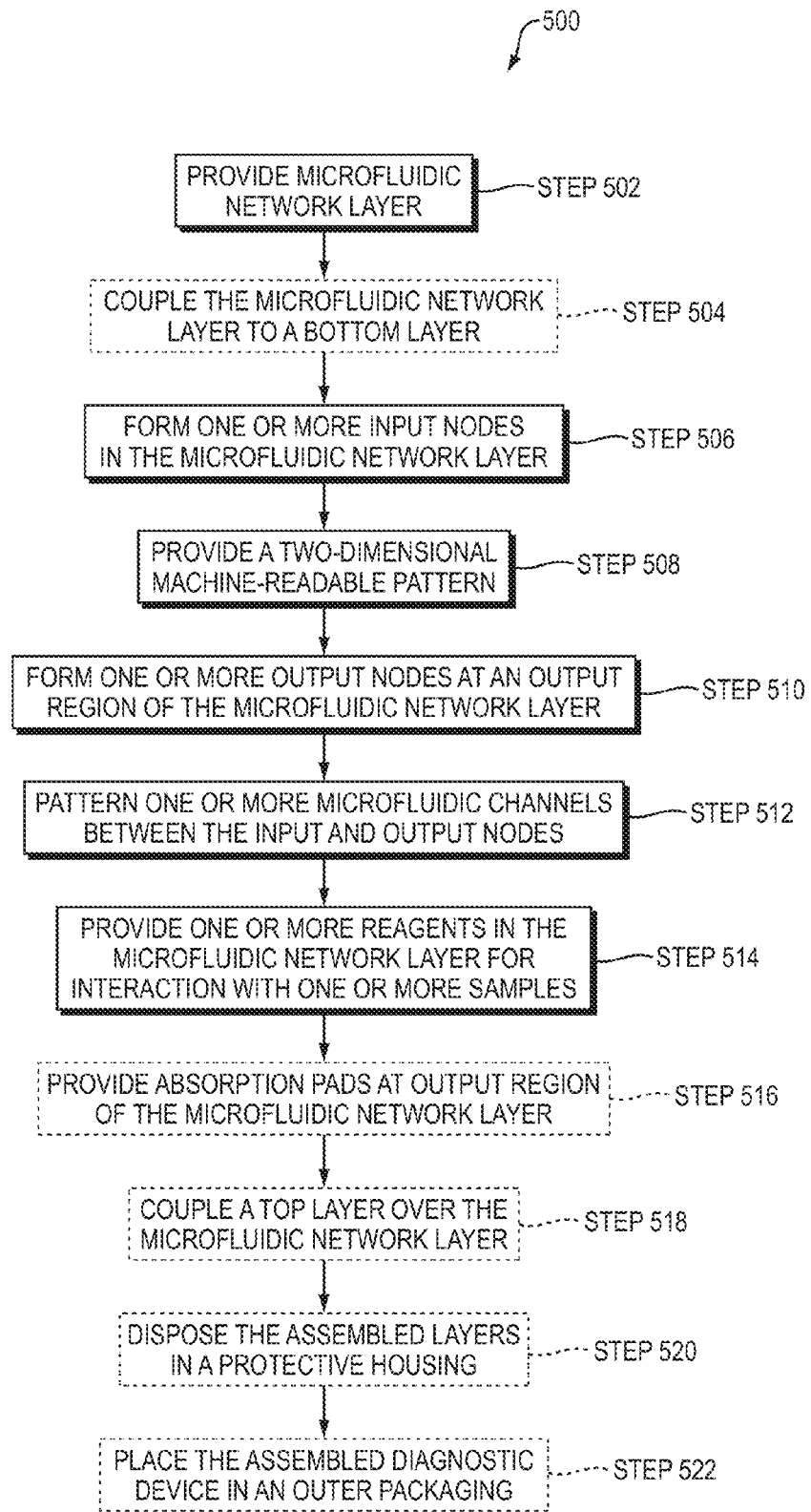
FIG. 5 is a flowchart illustrating an exemplary method for forming or fabricating the exemplary diagnostic device of FIGS. 2A-2E.

FIG. 5 is a flowchart illustrating an exemplary method 500 for forming or fabricating an exemplary diagnostic device. In step 502, one or more microfluidic network layers are provided for conducting one or more samples. The microfluidic network layer may be formed of any suitable material including, but not limited to, paper-based or paper-type materials (e.g., nitrocellulose), plastic, glass, any combination of the aforementioned materials, and the like.

In step 504, in an exemplary embodiment, the microfluidic network layer may be coupled to a bottom layer that is impermeable to and does not conduct the samples. Providing the microfluidic network layer on the bottom layer may prevent leaking of the samples from the diagnostic device.

In step 506, one or more input nodes may be formed in the microfluidic network layer for introducing one or more samples to the diagnostic device. The input nodes may be configured in any suitable arrangement including, but not limited to, linear, circular, ring-shaped, rectangular, matrix, random arrangements, and the like.

In step 508, a two-dimensional machine-readable pattern may be provided at an output region of the diagnostic device. In an exemplary embodiment, the pattern may be etched or printed directly on a portion of the microfluidic network layer. In another exemplary embodiment, the pattern may be provided on a stencil that is disposed above a portion of the microfluidic network layer.

In step 510, one or more output nodes may be formed in the microfluidic network layer so that the output nodes fall within the scope of the two-dimensional machine-readable pattern. In an exemplary embodiment in which the pattern is etched or printed directly on the microfluidic network layer, the pattern may include one or more empty portions (i.e., portions lacking etchings or printings). The output nodes may be configured and positioned at the empty portions so that display or non-display of visual indicators at the output nodes determines the final appearance of the two-dimensional machine-readable pattern. In another exemplary embodiment in which the pattern is provided on a stencil disposed over the microfluidic network layer, one or more apertures may be provided in the stencil. The output nodes in the microfluidic network layer may be aligned with the apertures in the stencil so that the output nodes are viewable by a user and so that the display or non-display of visual indicators at the output nodes determines the final appearance of the two-dimensional machine-readable pattern.

In step 512, one or more microfluidic channels may be patterned in the microfluidic network layer to extend between at least one input node and at least one output node. Any suitable technique may be used to create the channels including, but not limited to, laser cutting, die punching, hand cutting, and the like.

In step 514, one or more reagents may be provided at one or more input nodes, one or more output nodes and/or one or more channels in the microfluidic network layer. Any suitable number of reagents may be provided to interact with one or more samples. For example, a first reagent may interact with a first marker in a first sample to generate a first visual indicator, a second reagent may interact with a second marker in the first sample to generate a second visual indicator, and a third reagent may interact with a first marker in a second sample to generate a third visual indicator. Any suitable technique may be used to provide or pattern the reagents in the network layer. Exemplary reagent patterning techniques are described in Hasenbank M. S., Edwards T., Fu E., Garzon R., Kosar T. F., Look M., Mashadi-Hossein A., Yager P., "Demonstrations of Multi-Analyte Patterning Using Piezoelectric Inkjet Printing of Multiple Layers," *Anal. Chim. Acta.*, 2008, 611(1):80-8, and Martinez A. W., Phillips S. T., Whitesides G. M., Carrilho E., "Diagnostics for the Developing World: Microfluidic Paper-Based Analytical Devices," *Anal. Chem.*, 2010, 82(1):3-10, the entire contents of which are incorporated herein in their entirety by reference.

In step 516, in an exemplary embodiment, one or more absorbent pads may be provided at or near the output nodes to direct a sample along the microfluidic channels to the output nodes, and to prevent leakage of the sample out of the output nodes. The absorbent pads may maintain the motive force acting on the sample in the network layer by absorbing fluid from the directional wicking channels after the sample passes the output nodes. The absorbent pads thereby act as "engines" of lateral flow of the sample and, at the same time, prevent leakage of the sample. In an exemplary embodiment, the absorbent pads may be formed of a paper-based material, e.g., nitrocellulose.

In step 518, in an exemplary embodiment, a top layer may be coupled to the top of the microfluidic network layer. In an exemplary embodiment, the top layer may be partly or fully opaque to prevent a user from viewing the mapping between the input nodes and output nodes. In another exemplary embodiment, the top layer may be partly or fully transparent.

In an exemplary embodiment, the top layer may not cover the input nodes in the microfluidic network layer. In another exemplary embodiment, the top layer may cover the input nodes and may include one or more apertures that are aligned with the input nodes provided in the microfluidic network layer. In an exemplary embodiment, the apertures may be open to the outside. In another exemplary embodiment, the apertures may be covered with removable covers, e.g., tabs, before use. In order to introduce samples, a user may remove one or more selected covers to access the corresponding input nodes.

In an exemplary embodiment, the top layer may cover the output region of the microfluidic network layer and may include one or more apertures that are aligned with the output region of the microfluidic network layer. In another exemplary embodiment, the top layer may not cover the output region of the microfluidic network layer.

In step 520, in an exemplary embodiment, the layered bottom layer, microfluidic network layer, optional stencil and top layer may be disposed in a protective housing of the diagnostic device. In an exemplary embodiment, registration apertures may be provided in the layers of the diagnostic device for easy alignment and assembly of the layers. In an exemplary embodiment, the layers of the diagnostic device may be laminated between clear protective film membranes to protect the layers and maintain them in a sterile state.

In step 522, in an exemplary embodiment, the assembled diagnostic device may be placed in a suitable outer packaging or overwrap.

Figure 6:
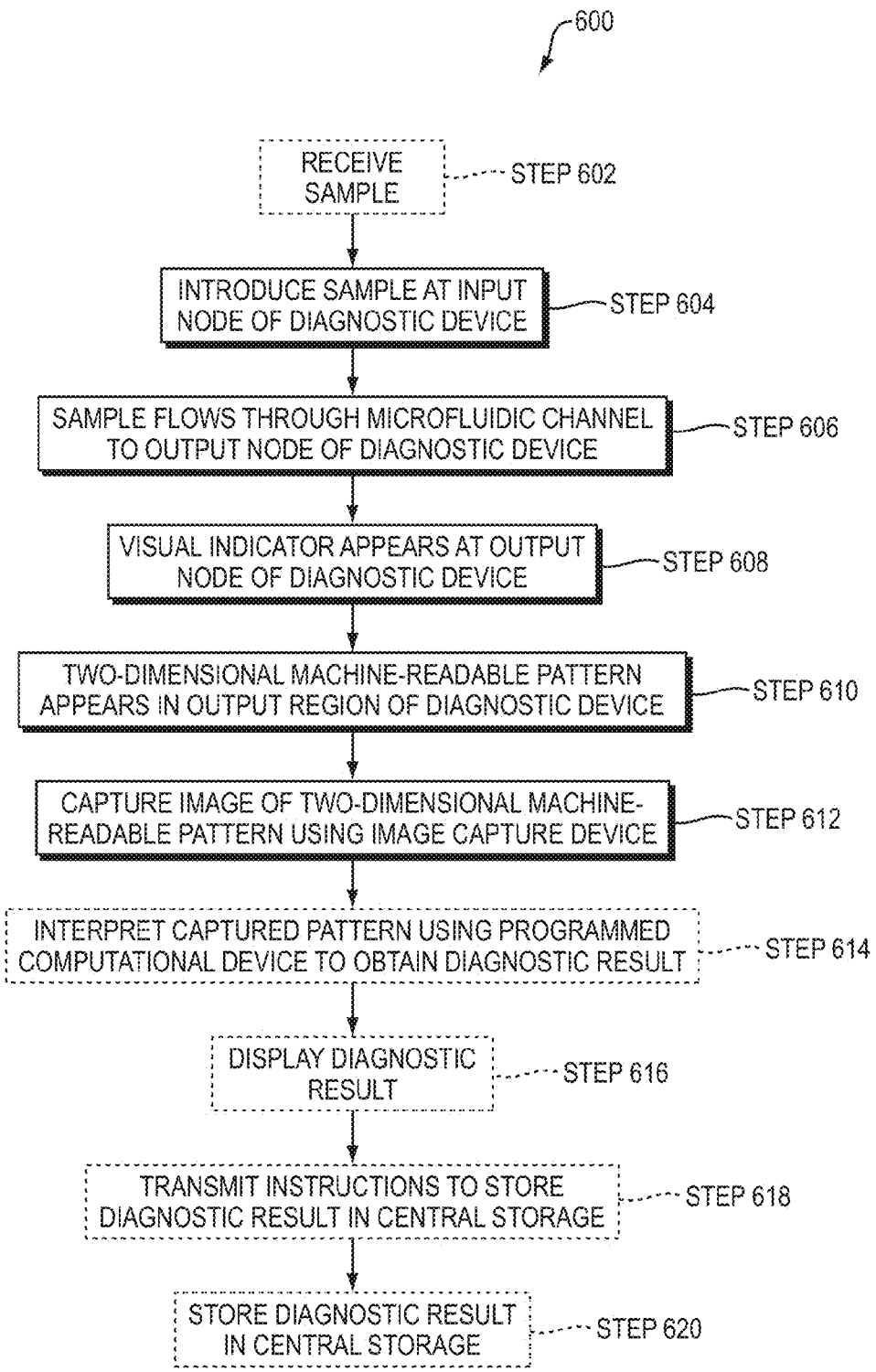
FIG. 6 is a flowchart illustrating an exemplary method for using the exemplary diagnostic device of FIGS. 2A-2E to detect a marker or characteristic in a sample.

FIG. 6 is a flowchart illustrating an exemplary method 600 for using an exemplary diagnostic device to detect the presence or absence of a marker or characteristic in a sample. In step 602, in an exemplary embodiment, a user of the diagnostic device may obtain or receive a sample.

In step 604, the user may introduce the sample at one or more input nodes in the diagnostic device. In an exemplary embodiment, a sample may be introduced to the diagnostic device as a suitable liquid sample, for example, a pure liquid, a combination or mixture of multiple liquids, a solution or mixture in a liquid (e.g., water, oil, etc.), a supernatant from a liquid suspension of solids, and the like. In an exemplary embodiment, a liquid sample may include particles, for example, nanoparticles, nanocrystals, nanomaterials, colloids and the like.

Any suitable number of samples may be introduced at any suitable number of input nodes in the diagnostic device. In an exemplary embodiment, a single sample or a combination of samples may be introduced at an input node. For example, a single blood sample may be introduced at a single input node, or a combination of two blood samples may be introduced at a single input node. In an exemplary embodiment, a sample may be introduced at more than one input node.

In step 606, the sample introduced at an input node may flow or wick along one or more microfluidic channels to one or more corresponding output nodes in the diagnostic device. In an exemplary embodiment in which the microfluidic channels are provided in a paper-based network layer, the sample may wick through the channels by capillary action without the use of or need for an external pump mechanism. As the sample flows through a channel, the sample may interact with one or more reagents provided at the input node, at one or more locations in the channel, and/or at the output nodes. In an exemplary embodiment, the sample interacts with a first set of one or more reagents along the channels and a second set of one or more reagents at the output nodes.

In step 608, the interaction of the sample with one or more reagents may result in the appearance of a visible indicator or a lack of a visible indicator at the corresponding output nodes. Any suitable visible indicator may appear at an output node of the diagnostic device. An exemplary visible indicator may be the appearance of a particular color at the output node that is different from the underlying color of the output node or the surrounding regions. For example, if the underlying color of the output node and the surrounding regions is white, then interaction of a sample with a reagent may result in the appearance of a pink color at the output node, indicating that the sample has a tested marker or characteristic. Another exemplary visible indicator may be the appearance of one or more alphanumeric characteristics at the output node. Another exemplary visible indicator may be the appearance of one or more pictorial symbols at the output node. Another exemplary visible indicator may be the combination of a color and one or more alphanumeric and/or pictorial symbols at the output node.

One of ordinary skill in the art will recognize that exemplary indicators appearing at an output region of a diagnostic device may be visual or non-visual. In an exemplary embodiment, the presence or absence of a marker in a sample may result in an electrochemical reaction or activity in the diagnostic device. For example, one or more output nodes in the diagnostic device associated with a marker may be electrochemically active if the marker is present in a sample, and may be electrochemically inactive if the marker is absent in the sample. An external reader may be used to detect the electrochemical activity of each output node in the matrix of diagnostic device. The electrochemical activity of the output nodes may be detected in sequence or in parallel by the reader. Exemplary electrochemical activity readers may include, but are not limited to, glucometers, multimeters, capacitive touch screens and other electrosensitive probes that operate at a point (e.g., to detect electrochemical activity at output nodes in sequence) or in a plane (e.g., to detect electrochemical activity at output nodes in parallel).

In step 610, the appearance or lack of visible indicators at one or more output nodes may result in the generation of a two-dimensional machine-readable pattern at an output region of the diagnostic device. An exemplary two-dimensional machine-readable pattern may take the form of a Quick Response (QR) code, a customized QR code, a matrix pattern, and the like.

In step 612, the two-dimensional machine-readable pattern appearing at the output region of the diagnostic device is read manually by a user or detected automatically by a suitable image capture device. Exemplary image capture devices may include, but are not limited to, a barcode scanner, tablet computer (e.g., the iPad™ tablet computer), mobile computing or communication device (e.g., the iPhone™ mobile communication device, the Android™ mobile communication device, and the like), a workstation, desktop computer, server, laptop, handheld computer, or other form of image capture, computing or telecommunications device that is capable of communication and that has sufficient processor power and memory capacity for capturing an image of the two-dimensional machine-readable pattern. In an exemplary embodiment, the user may capture an image of the two-dimensional pattern using a mobile camera phone.

In step 614, in an exemplary embodiment, the image capture device may perform computational or image analysis of the captured image to interpret the two-dimensional machine-readable pattern. Interpretation of the two-dimensional machine-readable pattern allows the device to automatically determine whether one or more markers or characteristics are present or absent in the sample. Exemplary embodiments may recognize the pattern in the image, compare the imaged pattern to a stored database of predefined patterns, and identify a diagnostic result corresponding to an identified pattern in the stored database. For example, if a first QR code appearing in the diagnostic device corresponds to the presence of sugar, the device may recognize the first QR code in the imaged pattern and may automatically determine that the sample contains sugar. Similarly, if a second QR code appearing in the diagnostic device corresponds to the presence of nitrites, the device may recognize the second QR code in the image pattern and may automatically determine that the sample contains nitrites. Similarly, a third QR code appearing in the diagnostic device corresponds to the presence of both sugar and nitrites, the device may recognize the third QR code in the imaged pattern and may automatically determine that the sample contains both sugar and nitrites.

In an exemplary embodiment, interpretation of the two-dimensional machine-readable pattern may also allow the device to automatically determine whether a secondary diagnostic condition exists in the sample or the user from whom the sample was derived. That is, an exemplary diagnostic device may be used to implement a marker panel in which one or more markers may be tested to determine whether a secondary diagnostic condition is indicated by the markers. For example, if one or more disease markers associated with a disease prognosis or disease state are detected in a sample (by interpretation of a corresponding first two-dimensional machine-readable pattern), exemplary embodiments may automatically determine additional information about the sample, for example, that the disease prognosis or disease state exists. In one example, if nitrites are detected in a urine sample (by interpretation of a corresponding second two-dimensional machine-readable pattern), exemplary embodiments may automatically determine a secondary diagnostic condition of a urinary tract infection. In another example, if the secreted non-structural protein 1 of a dengue virus (sNS1) and the IgG and IgM antibodies are detected simultaneously in a sample (by interpretation of a corresponding second two-dimensional machine-readable pattern), exemplary embodiments may automatically determine the presence of a dengue virus as well as the onset of the physiological response the dengue virus.

In some cases, the degree of interaction between the sample and the reagents in the diagnostic device may affect the intensity of the visible indicators at the output nodes. For example, a larger amount, volume, concentration or strength of a marker in the sample may result in a higher intensity of the visual indicator, and vice versa. Exemplary embodiments may detect the intensity of a visible indicator at an output node to quantitatively determine the degree or extent of a marker or characteristic in the sample. For example, a darker colored indicator at an output node corresponding to creatine may be analyzed to quantitatively determine that a high level of creatine is present in a urine sample. Conversely, a lighter colored indicator at an output node corresponding to creatine may be analyzed to quantitatively determine that a low level of creatine is present in a urine sample.

In an exemplary embodiment, the qualitative and/or quantitative determination of a marker or characteristic in a sample may be used to make a secondary determination of, for example, a diagnostic condition associated with the sample or the user from which the sample was obtained. For example, in checking urine creatine levels for a drug test, detection of a creatine level in a urine sample that is lower than a predetermined threshold may indicate that an associated drug test may have been manipulated by the user.

In an exemplary embodiment, an image capture device that captures an image of the two-dimensional machine-readable pattern may also interpret the two-dimensional pattern. In another exemplary embodiment, an image capture device that captures an image of the two-dimensional machine-readable pattern may not itself interpret the two-dimensional pattern, but may transmit it to another computational device or to a user for interpretation of the two-dimensional pattern. In this exemplary embodiment, the computational device that performs the interpretation may be provided with the image capture device, may be coupled to the image capture device, or may be provided remotely from the image capture device.

The capture and interpretation of the two-dimensional machine-readable pattern in an exemplary diagnostic device allow for rapid point-of-care detection of markers and characteristics of interest in samples. This detection and interpretation may be accomplished in an efficient manner using exemplary diagnostic devices without the need for specialized equipment or training. This allows exemplary diagnostic devices to detect and analyze samples at a faster rate compared to conventional centralized lab assays that require special equipment, training and reagents.

In step 616, in an exemplary embodiment, one or more results associated with the two-dimensional machine-readable pattern may be displayed at a visual display device, for example, at the location of the user or remotely from the user (e.g., at a hospital that is remote from the diagnostic device and from the user). Exemplary displayed results may include, but are not limited to, the two-dimensional machine-readable pattern itself, the presence or absence a marker or characteristic of the sample corresponding to the two-dimensional pattern, a secondary diagnostic condition associated with the sample, the source of the sample (e.g., an identification of the person from whom the sample was derived), an identification of the diagnostic device, a geographical location of the diagnostic device (e.g., using a GPS device provided in or with the diagnostic device), the date and time of use of the diagnostic device, and the like. In an exemplary embodiment, a two-dimensional machine-readable pattern corresponding to a particular user may be associated with an identifier for the user. For example, a two-dimensional pattern generated in the user's device may be encoded to include an identifier for the user. In another example, a combined result may include the two-dimensional pattern and an identifier for the user.

In step 618, in an exemplary embodiment, instructions may be sent to store one or more results associated with the two-dimensional machine-readable pattern in a central storage, for example, a central server, a central database, and the like. In step 620, in an exemplary embodiment, one or more results associated with the two-dimensional machine-readable pattern may be stored in the central storage. In an exemplary embodiment, the central storage may store user-specific results obtained from multiple diagnostic device used by a single user. In another exemplary embodiment, the central storage may store distributed results obtained from multiple diagnostic devices used by multiple users. The users may be located at the same or at different geographical locations.

The central storage may be updated with real-time diagnostic data for a population of people distributed over a geographical area. The real-time and central nature of the exemplary diagnostic data storage allows rapid point-of-care detection of pathogens that threaten supplies of food, water and blood. Food-borne diseases result in many millions of dollars of health care costs. According to the United States Department of Agriculture (USDA), about 6.5 to 33 million people in the United States contract food-borne illnesses every year. The estimated medical costs and productivity losses range from about $6 to $34 billion a year.

Multiple exemplary diagnostic devices distributed to multiple users enable broad and real-time surveillance of diseases and pathogens and their early detection. This allows for rapid crowdsourcing of diagnostic results that may allow epidemiological examination and detection of pathogens and disease conditions spread over a population and/or a geographical area. Broad-based use of exemplary diagnostic devices may also enable early localization of infected areas via, for example, mobile phone reporting and geographic information system (GIS) mapping.

In an exemplary embodiment, broad-based use of exemplary diagnostic devices may allow aggregation of diagnostic data from multiple users to generate a profile of diagnostic data for a particular geographical location or a particular demographic group. For example, a "health map" may be generated based on data received from the diagnostic devices of multiple users. An exemplary "health map" is advantageous over conventional health data reports that aggregate health data received from news reports and word-of-mouth. In contrast to these conventional health data reports, an exemplary "health map" is generated based on real-time actual diagnostic results, instead of the less specific and less accurate clinical case reporting used in generating conventional health data aggregates. Exemplary "health maps" thus allow more reliable and accurate field diagnostic data collection and analysis.

Furthermore, exemplary diagnostic devices allow detection of prognostic biomarkers in a biological sample obtained from a patient that reflect disease severity. Prognosis prediction is a significant medical challenge, and military and civilian medical personnel have a pressing need to identify patients at high risk of sudden death or progression to life-threatening disease states. An exemplary diagnostic device may be used to detect one or more biomarkers associated with a high risk of sudden death or progression to very serious disease states. Detection of these biomarkers in an exemplary diagnostic device may allow real-time alerting of medical personnel as to the severity of a patient's disease or the risk of death. For example, the diagnostic device or a communication device associated with the diagnostic device may be used to transmit an alert message or signal to medical personnel upon detection of the relevant biomarkers.

III. SECOND NON-LIMITING EXEMPLARY DIAGNOSTIC DEVICE

Exemplary diagnostic devices may be used to ensure user compliance with medication and/or testing protocols. Many patients who are on medication regimens fail to take their medications as prescribed by their doctors. Non-compliance to medication protocols results in poorer health outcomes, excess hospitalizations and avoidable medical spending. Non-compliance also results in suboptimal prescribing, drug administration and diagnosis. In developing countries, for example, treatment regimens for diseases such as tuberculosis (TB), malaria, diabetes and heart disease and basic antibiotic treatments create significant non-compliance problems. Non-compliance with TB medication regimens contributes to patient morbidity, mortality and a rise in multiple drug resistance (MDR) TB.

Directly observed therapy short-course (DOTS) is a conventional protocol for monitoring and ensuring compliance with medication regimens. DOTS involves in-person observation of the administration of each dose of a medication by healthcare personnel, a process that may become prohibitively costly. Community-based DOTS (CB-DOTS) is another conventional protocol that involves in-person observation of the administration of each dose of a medication by trained members of a community. Although the use of trained community members can help in reducing the cost of compliance monitoring, community programs vary considerably in their quality. Furthermore, a large proportion of the world population lives in areas that are not covered by or are insufficiently covered by DOTS protocols.

Exemplary embodiments address the deficiencies in DOTS protocols by providing diagnostic devices and systems for detecting the presence or absence of one or more markers in one or more samples. The presence or absence of one or more markers in a sample may further be used to determine whether a patient has a particular condition, e.g., whether the patient has taken a medication, whether the patient is following the correct protocol for a drug testing regimen, whether the patient has a disease, whether the patient is intoxicated, and the like. Exemplary samples usable in exemplary embodiments may include, but are not limited to, blood, blister exudate, urine, sweat, saliva, other bodily fluids. Exemplary markers testable in exemplary embodiments may include, but are not limited to, the presence or absence of a biomarker, tracer or metabolite of a medication.

Exemplary embodiments provide methods for monitoring the compliance of a patient with a medication or testing regimen, e.g., whether the patient is taking doses of a medication at scheduled times, whether the patient is following the correct protocol for a drug-testing regimen, and the like. In an exemplary embodiment, exemplary methods may provide one or more rewards to the patient for complying with the regimen. In an exemplary embodiment, exemplary methods may provide one or more penalties to the patient for failing to comply with the regimen. Exemplary embodiments are usable for monitoring and ensuring patient compliance to treatment regimens for any suitable medication including, but not limited to, medications for tuberculosis (TB), malaria, diabetes, heart disease, bacterial infections, and the like.

Figure 7:
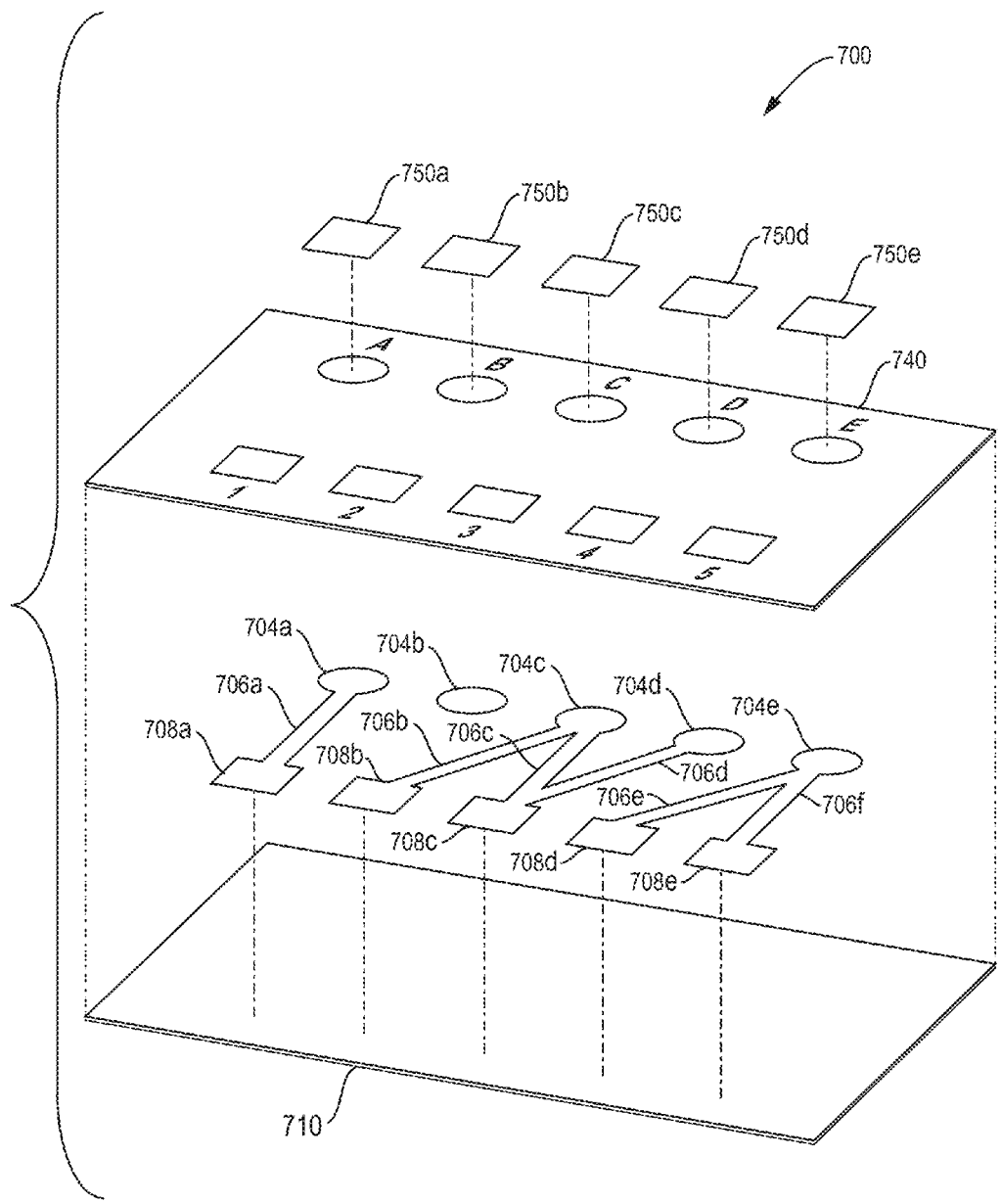
FIG. 7 illustrates an exploded view of an exemplary diagnostic device provided in accordance with exemplary embodiments.

FIG. 7 illustrates an exploded view of an exemplary diagnostic device 700 in which the different layers of the device are separated for easier viewing. A bottom layer 710 may be provided in the diagnostic device 700 to support one or more layers disposed above it. The bottom layer 710 may be impermeable to samples and may prevent the samples from leaking from the diagnostic device 700. In an exemplary embodiment, the bottom layer 710 may be formed of contact paper with the adhesive surface facing up or toward a network layer.

One or more network layers may be provided above the bottom layer 710 in order to conduct one or more samples. In an exemplary embodiment, the network layer may be a paper-based microfluidic circuit formed of filter paper. The porosity of the filter paper may facilitate the flow of fluids through the network.

The network layer may include a set of one or more input nodes, a set of one or more output nodes and one or more channels connecting at least one input node to at least one output node. The channels may be substantially two-dimensional or three-dimensional. The channels may have exemplary widths ranging from about a millimeter to several millimeters. For example, the network layer may include input nodes 704a, 704b, 704c, 704d, 704e, and output nodes 708a, 708b, 708c, 708d, 708e. Input node 704a may be in fluid communication with output node 708a via channel 706a. Input node 704b may not be in fluid communication with any output node. Input node 704c may be in fluid communication with output node 708b via channel 706b and with output node 708c via channel 706c. Input node 704d may be in fluid communication with output node 708c via channel 706d. Input node 704e may be in fluid communication with output node 708d via channel 706e and with output node 708e via channel 706f. Similar configurations may be provided in the network layers 702b and 702c. The network layer may include reagents at the input nodes, the output nodes and/or the channels, for detecting the presence or absence of one or more markers in one or more samples. The reagents may be embedded in the network layer or may coat components of the network layer.

The input nodes 704a, 704b, 704c, 704d, 704e in the network layer are configured to allow introduction of one or more samples to the diagnostic device 700. Each input node may be identified by a visual identifier visible to the user at all times including, but not limited to, a number, a set of numbers, a letter, a set of letters, a symbol, a color, or any combination thereof. In an exemplary embodiment, each input node is identified by a unique identifier. For example, in the exemplary embodiment illustrated in FIG. 7, the five exemplary input nodes have associated identifiers "A," "B," "C," "D," "E," respectively. In the exemplary embodiment illustrated in FIG. 7, the input nodes are organized linearly along a straight line. In other exemplary embodiments, the input nodes may be organized in any suitable configuration, e.g., circular arrangements, oval arrangements, wavy arrangements, rectangular arrangements, random arrangements, scattered arrangements, and the like.

The output nodes 708a, 708b, 708c, 708d, 708e in the network layer are configured to display one or more visual indicators due to the interaction of markers in the samples with one or more reagents. In the exemplary embodiment illustrated in FIG. 7, the output nodes 708a, 708b, 708c, 708d, 708e are organized linearly along a straight line. In other exemplary embodiments, the output nodes 708a, 708b, 708c, 708d, 708e may be organized in any suitable configuration, e.g., circular arrangements, oval arrangements, wavy arrangements, rectangular arrangements, random arrangements, scattered arrangements, and the like. In an exemplary embodiment, the numbers of input nodes 704a, 704b, 704c, 704d, 704e and output nodes 708a, 708b, 708c, 708d, 708e may be the same. In another exemplary embodiment, the numbers of input nodes and output nodes may be different.

In an exemplary embodiment, each output node may include a hidden indicator or code that is revealed only when the presence or absence of a marker is detected in the sample. In an exemplary embodiment, one or more markers in the sample may react chemically or biologically with the reagents. The reaction may be a colorimetric reaction and may cause a color change at the output node that may reveal a hidden code. In other exemplary embodiments, other types of interactions (e.g., electrochemical interactions) may take place between the marker in the sample and the reagents.

The hidden codes may include, but are not limited to, a number, a set of numbers, a letter, a set of letters, a symbol, a color, or any combination thereof. The hidden codes associated with different output nodes in the device may be the same or different. In an exemplary embodiment, each output node may have a different associated hidden code. When a set of one or more hidden codes is revealed at one or more output nodes, the combination of the revealed codes may collectively form a "combination code."

A top layer 740 may be provided to cover the network layer to prevent the user from viewing the mapping between the input nodes 704a, 704b, 704c, 704d, 704e and the output nodes 708a, 708b, 708c, 708d, 708e in the network layer. In an exemplary embodiment, apertures A, B, C, D, E may be provided in the top layer 740 aligned with the input nodes 704a, 704b, 704c, 704d, 704e, respectively. In an exemplary embodiment, removable covers or tabs may 750a, 750b, 750c, 750d, 750e may be used to cover the apertures A, B, C, D, E before use of the device. A user may selectively remove one or more covers 750a, 750b, 750c, 750d, 750e to access corresponding input nodes. The removable covers 750a, 750b, 750c, 750d, 750e provide a user-activated valve mechanism to select one or more input nodes 704a, 704b, 704c, 704d, 704e, and thereby the channels that are activated at any given time. This provides a switching or valving mechanism by which a user may selectively make connections in the diagnostic device.

In an exemplary embodiment, a user may punch out certain input nodes and/or channels to select activation points in an inverse fashion by blocking access to the punched-out input nodes and/or channels. One or more removable tabs may be provided in the input nodes and/or channels to enable the user to remove material from the input nodes and/or the channels. For example, removal of a tab may result in the removal of material from a corresponding input node or channel, thereby breaking the connection between the input node and an output node. This provides a switching or valving mechanism by which a user may selectively break connections in the diagnostic device.

Similarly, in an exemplary embodiment, apertures 1, 2, 3, 4, 5 may be provided in the top layer 740 aligned with the output nodes 708a, 708b, 708c, 708d, 708e, respectively, to allow a user to view the output nodes. In an exemplary embodiment, the removable covers may be removed by the patient to expose the output nodes 708a, 708b, 708c, 708d, 708e for detecting the appearance of any hidden codes at the output nodes.

In the exemplary device 700, different mapping schemes may be implemented using the channels provided between the input nodes and the output nodes. In an exemplary embodiment, the channels may provide fluid communication between at least one input node and at least one output node.

The mapping scheme between the input nodes and the output nodes may be random or non-random. In an exemplary embodiment, exemplary mapping schemes may include mapping of one or more input nodes, each to a single output node; mapping of one or more output nodes, each to a single input node; mapping of one or more input nodes, each to two or more output nodes; mapping of one or more output nodes, each to two or more input nodes; mapping of two or more output nodes to a single input node; mapping of two or more input nodes to a single output node; not mapping one or more input nodes to any output node; not mapping one or more output nodes to any input node; mapping a single input node to a single output node; and the like. Any combination of one or more of these mapping schemes may be present in an exemplary diagnostic device. Cross-mapping of an input node to multiple output nodes allows detection of multiple markers at the different output nodes.

One of ordinary skill in the art will recognize that the mapping between input and output nodes shown in FIG. 7 is merely illustrative and that any suitable mapping scheme may be implemented in exemplary embodiments.

In an exemplary embodiment, a complex mapping scheme is provided between the input nodes and the output nodes that is non-obvious to a user and is hidden from the view of the user by the top layer 740. This prevents the user from guessing which hidden codes may be revealed from introduction of the sample to a selected set of input nodes. The mapping of the input nodes to the output nodes may be known to a supervising entity that monitors a user's compliance with a medication regimen. Thus, the supervising entity knows the combination code associated with a particular set of input nodes, but the user may not know the combination code associated with a set of input nodes prior to the combination code being revealed at the output nodes. Thus, the hidden mapping between the input nodes and output nodes provides encryption of the diagnostic mechanism to the user of the device, such that the user cannot predict which hidden codes will be revealed in response to introduction of the sample at a particular set of input nodes.

An exemplary diagnostic device may include one or more die markers at the input nodes, the output nodes and/or the channels. A sample taking two different channels between input and output nodes may result in differently colored codes at the output nodes if the channels contain different die markers. The placement of the die markers may be hidden from the user and, as such, the colors that appear at the output nodes may also be used as part of the combination code. In an exemplary embodiment, introduction of a sample at a particular set of input nodes may reveal a combination code consisting of a set of codes and colors at one or more output nodes. For example, in the exemplary embodiment of FIG. 7, a sample introduced at input node 704c may pick up a first die marker in channel 706b to result in a purple-colored code at output node 708b, while a sample introduced at input node 704d may pick up a different second die marker in channel 706c to result in a blue-colored code at output node 708c.

In an exemplary embodiment, the indicator appearing at an output node may depend on other variables including, but not limited to, the type of the sample used (e.g., saliva, urine, sweat, blood, blister exudate, and the like), the type of marker that interacts with the reagents in the device (e.g., sugar, medication, hormone, and the like).

In an exemplary embodiment in which the diagnostic device is used to detect the presence or absence of a marker in a sample, one or more output nodes may include hidden codes that are revealed when the marker, if present in the sample, interacts with the reagents in the device. In another exemplary embodiment in which the diagnostic device is used to detect the presence or absence of two or more markers in a sample, different sets of output nodes may include hidden codes that are revealed when the different markers, if present in the sample, interact with the reagents in the device. For example, a first set of output nodes (e.g., output nodes 708a, 708b) may include hidden codes that are revealed when a drug metabolite is present in a patient's urine, and a second set of output nodes (e.g., output nodes 708c, 708d) may include hidden codes that are revealed when a sugar is present in a patient's urine.

In an exemplary embodiment, a sample (e.g., the patient's blood, blister exudate, saliva, urine, sweat, and the like) may be used to determine whether a patient has a secondary condition (e.g., whether the patient has taken a particular medication, whether the patient has a particular physical condition like a disease, and the like). The one or more reagents present in an exemplary diagnostic device may react with one or more markers in the sample to indicate whether the patient has the secondary condition. In an exemplary embodiment, the condition may be diagnosed based on the presence or absence of a single marker in the sample. In another exemplary embodiment, the condition may be diagnosed based on the presence or absence of two or more markers in the sample. In another exemplary embodiment, one or more sample may be tested to determine whether a patient has two or more conditions (e.g., whether the patient has multiple diseases, whether the patient has a disease and whether the patient has taken a medication, whether the patient has taken two medications, whether the patient is intoxicated and has taken a medication).

Figure 8:
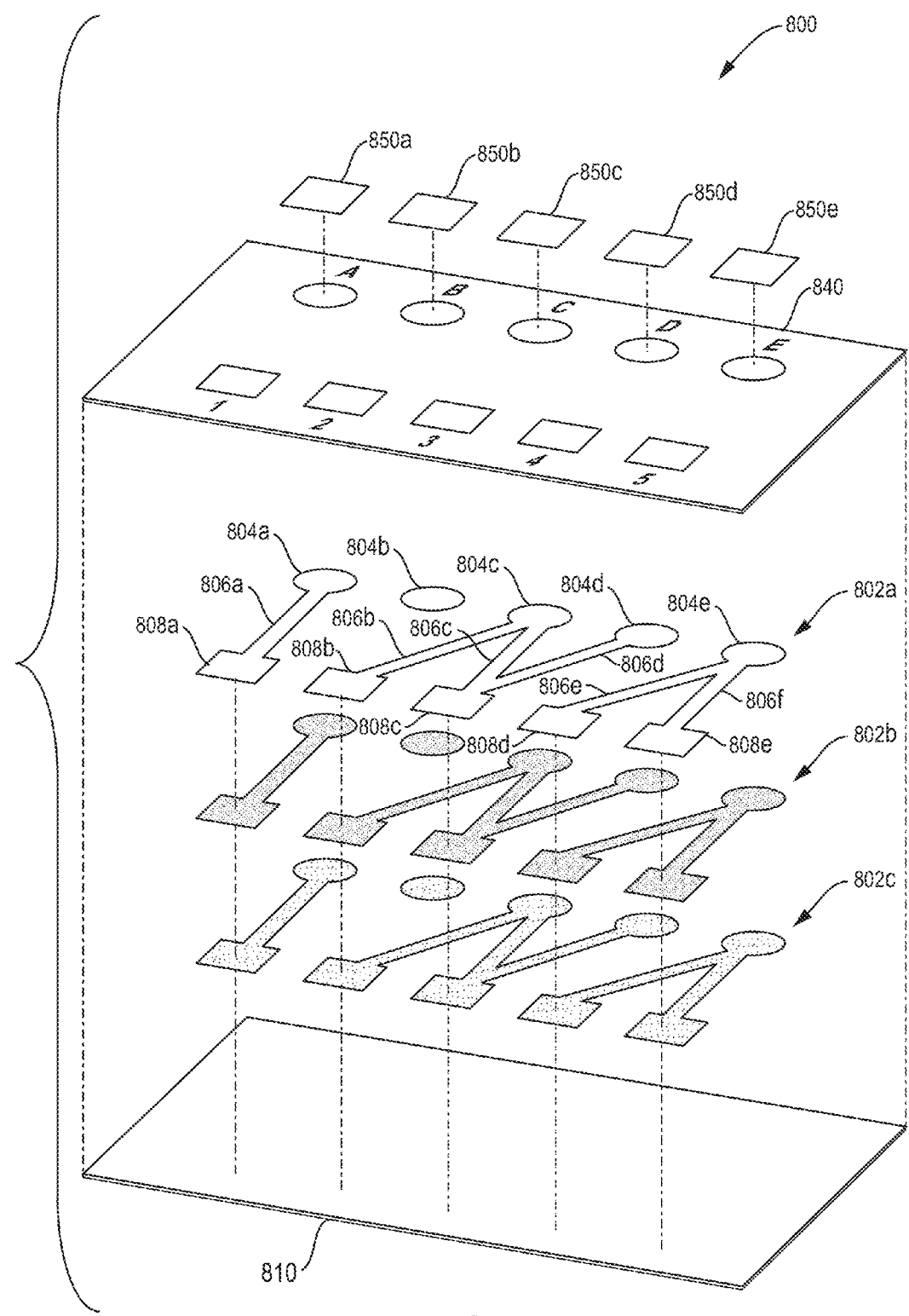
FIG. 8 illustrates an exploded view of another exemplary diagnostic device provided in accordance with exemplary embodiments.

FIG. 8 illustrates an exploded view of another exemplary diagnostic device 800 in which the different layers of the device are separated for easier viewing. The device 800 includes multiple stacked microfluidic network layers. A bottom layer 810 may be provided in device 800 to support one or more layers disposed above it. Two or more network layers, e.g., layers 802a, 802b, 802c, may be provided above the bottom layer 810 in order to conduct one or more samples. The network layers 802a, 802b, 802c may be configured in a stacked manner or may be disposed adjacent to each other.

Each network layer 802a, 802b, 802c may include a set of one or more input nodes, a set of one or more output nodes and one or more channels connecting at least one input node to at least one output node. For example, the network layer 802a may include input nodes 804a, 804b, 804c, 804d, 804e, and output nodes 808a, 808b, 808c, 808d, 808e. Input node 804a may be in fluid communication with output node 808a via channel 806a. Input node 804b may not be in fluid communication with any output node. Input node 804c may be in fluid communication with output node 808b via channel 806b and with output node 808c via channel 806c. Input node 804d may be in fluid communication with output node 808c via channel 806d. Input node 804e may be in fluid communication with output node 808d via channel 806e and with output node 808e via channel 806f. Similar configurations may be provided in the network layers 802b and 802c.

The network layers 802a, 802b, 802c may each include reagents at the input nodes, the output nodes and/or the channels, for detecting the presence or absence of one or more markers in one or more samples. In an exemplary embodiment, the different network layers 802a, 802b and 802c may include different sets of reagents that may react with a sample in a specific reaction order. The different reactions may provide an additional combinatorial scheme in the codes that may appear in the output nodes.

Above the network layers 802a 802b, 802c, a top layer 840 may be provided to cover the channels of the network layers. In an exemplary embodiment, apertures A, B, C, D, E may be provided in the top layer 840 aligned with the input nodes 804a, 804b, 804c, 804d, 804e, respectively. In an exemplary embodiment, removable covers or tabs may 850a, 850b, 850c, 850d, 850e may be used to cover the apertures A, B, C, D, E before use of the device. A user may selectively remove one or more covers 850a, 850b, 850c, 850d, 850e to access corresponding input nodes. This provides a switching or valving mechanism by which a user may selectively make connections in the diagnostic device. Similarly, in an exemplary embodiment, apertures 1, 2, 3, 4, 5 may be provided in the top layer 840 aligned with the output nodes 808a, 808b, 808c, 808d, 808e, respectively, to allow a user to view the output nodes.

In an exemplary embodiment, a user may punch out certain input nodes and/or channels to select activation points in an inverse fashion by blocking access to the punched-out input nodes and/or channels. One or more removable tabs may be provided in the input nodes and/or channels to enable the user to remove material from the input nodes and/or the channels. For example, removal of a tab may result in the removal of material from a corresponding input node or channel, thereby breaking the connection between the input node and an output node. This provides a switching or valving mechanism by which a user may selectively break connections in the diagnostic device.

Components of the exemplary diagnostic device 800 of FIG. 8 similar or common to the exemplary diagnostic device 700 of FIG. 7 are described in connection with FIG. 7.

Figure 9:
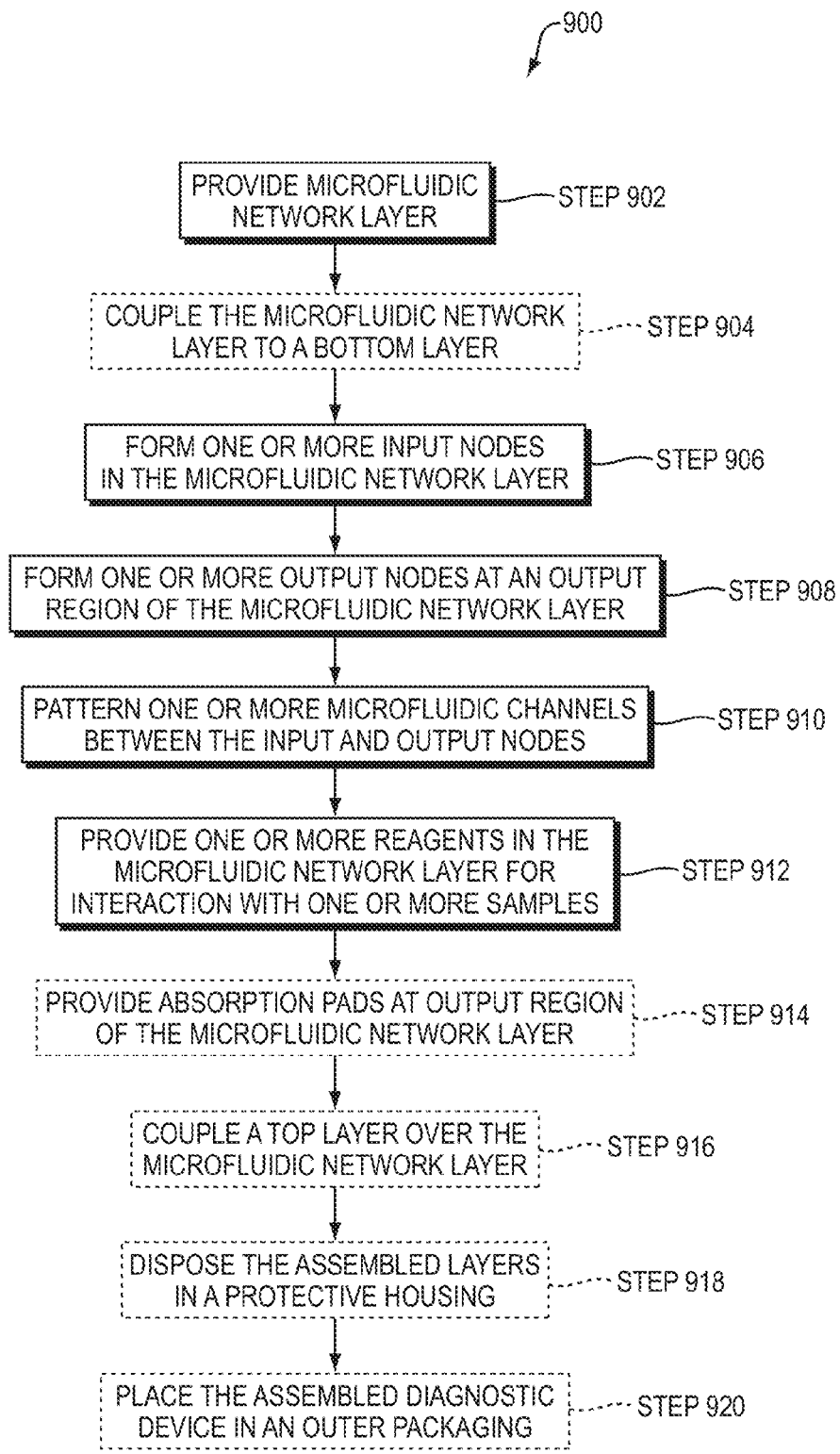
FIG. 9 is a flowchart illustrating an exemplary method for forming or fabricating the exemplary diagnostic device of FIGS. 7 and 8.

FIG. 9 is a flowchart illustrating an exemplary method 900 for forming or fabricating an exemplary diagnostic device. In step 902, one or more microfluidic network layers are provided for conducting one or more samples. The microfluidic network layer may be formed of any suitable material including, but not limited to, paper-based or paper-type materials (e.g., nitrocellulose), plastic, glass, any combination of the aforementioned materials, and the like.

In step 904, in an exemplary embodiment, the microfluidic network layer may be coupled to a bottom layer that is impermeable to and does not conduct the samples. Providing the microfluidic network layer on the bottom layer may prevent leaking of the samples from the diagnostic device.

In step 906, one or more input nodes may be formed in the microfluidic network layer for introducing one or more samples to the diagnostic device. The input nodes may be configured in any suitable arrangement including, but not limited to, linear, circular, ring-shaped, rectangular, matrix, random arrangements, and the like.

In step 908, one or more output nodes may be formed at an output region of the microfluidic network layer.

In step 910, one or more microfluidic channels may be patterned in the microfluidic network layer to extend between at least one input node and at least one output node. Any suitable technique may be used to create the channels including, but not limited to, laser cutting, die punching, hand cutting, and the like.

In step 912, one or more reagents may be provided at one or more input nodes, one or more output nodes and/or one or more channels in the microfluidic network layer. Any suitable number of reagents may be provided to interact with one or more samples. For example, a first reagent may interact with a first marker in a first sample to generate a first visual indicator, a second reagent may interact with a second marker in the first sample to generate a second visual indicator, and a third reagent may interact with a first marker in a second sample to generate a third visual indicator. Any suitable technique may be used to provide or pattern the reagents in the network layer. Exemplary reagent patterning techniques are described in Hasenbank M. S., Edwards T., Fu E., Garzon R., Kosar T. F., Look M., Mashadi-Hossein A., Yager P., "Demonstrations of Multi-Analyte Patterning Using Piezoelectric Inkjet Printing of Multiple Layers," *Anal. Chim. Acta.,* 2008, 611(1):80-8, and Martinez A. W., Phillips S. T., Whitesides G. M., Carrilho E., "Diagnostics for the Developing World: Microfluidic Paper-Based Analytical Devices," *Anal. Chem.,* 2010, 82(1):3-10, the entire contents of which are incorporated herein in their entirety by reference.

In step 914, in an exemplary embodiment, one or more absorbent pads may be provided at or near the output nodes to direct a sample along the microfluidic channels to the output nodes, and to prevent leakage of the sample out of the output nodes. The absorbent pads may maintain the motive force acting on the sample in the network layer by absorbing fluid from the directional wicking channels after the sample passes the output nodes. The absorbent pads thereby act as "engines" of lateral flow of the sample and, at the same time, prevent leakage of the sample. In an exemplary embodiment, the absorbent pads may be formed of a paper-based material, e.g., nitrocellulose.

In step 916, in an exemplary embodiment, a top layer may be coupled to the top of the microfluidic network layer. In an exemplary embodiment, the top layer may be partly or fully opaque to prevent a user from viewing the mapping between the input nodes and output nodes. In another exemplary embodiment, the top layer may be partly or fully transparent.

In an exemplary embodiment, the top layer may not cover the input nodes in the microfluidic network layer. In another exemplary embodiment, the top layer may cover the input nodes and may include one or more apertures that are aligned with the input nodes provided in the microfluidic network layer. In an exemplary embodiment, the apertures may be open to the outside. In another exemplary embodiment, the apertures may be covered with removable covers, e.g., tabs, before use. In order to introduce samples, a user may remove one or more selected covers to access the corresponding input nodes.

In an exemplary embodiment, the top layer may cover the output region of the microfluidic network layer and may include one or more apertures that are aligned with the output region of the microfluidic network layer. In another exemplary embodiment, the top layer may not cover the output region of the microfluidic network layer.

In step 918, in an exemplary embodiment, the layered bottom layer, microfluidic network layer, optional stencil and top layer may be disposed in a protective housing of the diagnostic device. In an exemplary embodiment, registration apertures may be provided in the layers of the diagnostic device for easy alignment and assembly of the layers. In an exemplary embodiment, the layers of the diagnostic device may be laminated between clear protective film membranes to protect the layers and maintain them in a sterile state.

In step 920, in an exemplary embodiment, the assembled diagnostic device may be placed in a suitable outer packaging or overwrap.

Figure 10:
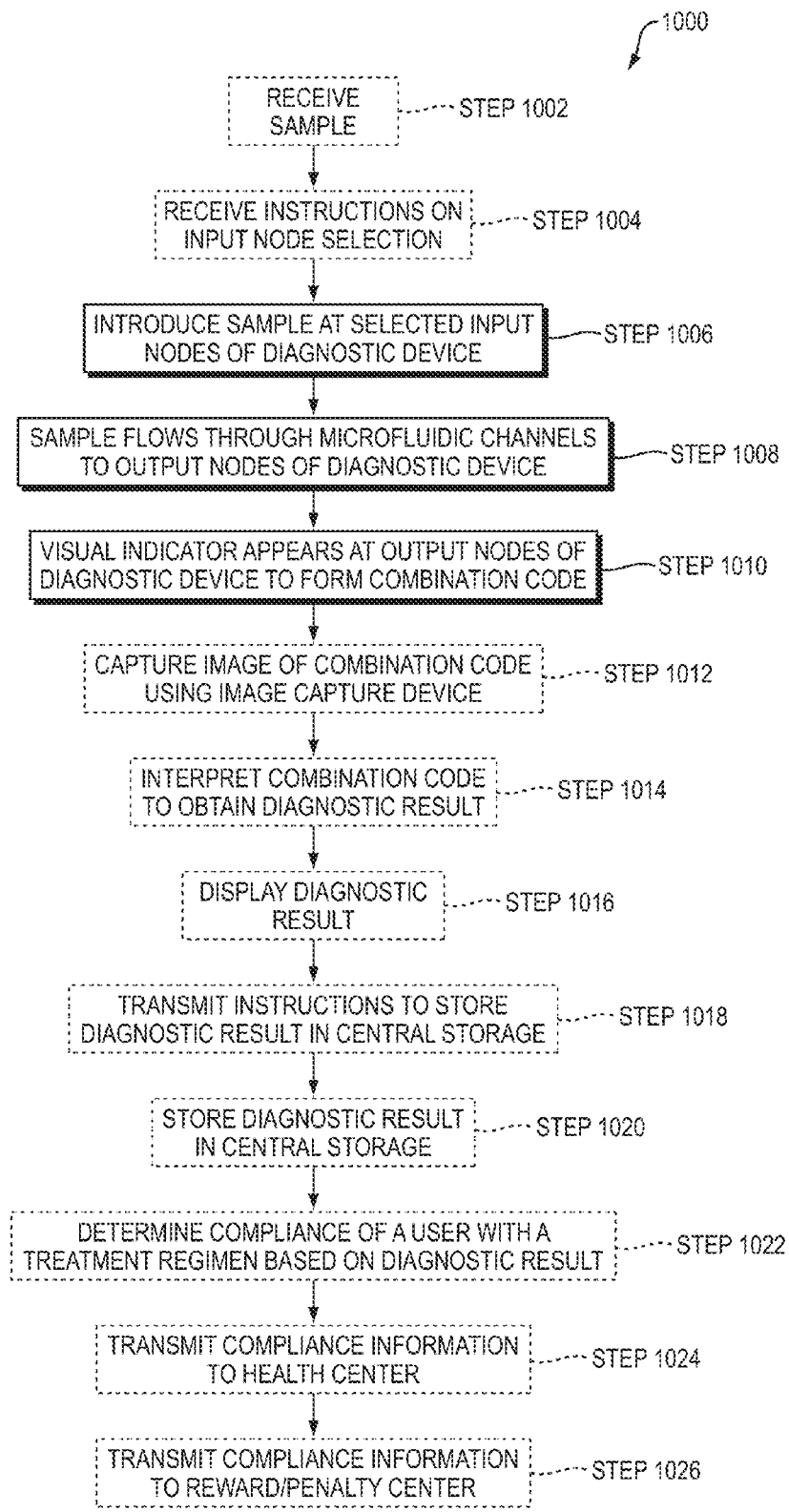
FIG. 10 is a flowchart illustrating an exemplary method for using the exemplary diagnostic devices of FIGS. 7 and 8.

FIG. 10 is a flowchart illustrating an exemplary method 1000 for using an exemplary diagnostic device to detect the presence or absence of a marker or characteristic in a sample. Exemplary method 1000 may also be used to determine whether a user is in compliance with a medication regimen.

In step 1002, in an exemplary embodiment, a user of the diagnostic device may obtain or receive one or more samples. In an exemplary embodiment, a reminder may be preset to remind the user to take a dose of a medication at a predetermined time. The reminder may be provided to the user by any suitable means including, but not limited to, a telephone call, message or alarm, an email message, a telephone text message, and the like. The user may obtain the sample after taking the dose of the medication.

In step 1004, an instruction may be provided to the user on using a set of one or more input nodes to test the sample. In an exemplary embodiment, the instruction may instruct the user to remove one or more removable tabs covering one or more input nodes of the diagnostic device, and to introduce the sample at the exposed input nodes, e.g., "Remove tabs A and C and introduce saliva sample at input nodes A and C."

The instruction may be formulated in a way that prevents the user from guessing the instruction ahead of time. The combination code that is expected to be generated if the user has taken a medication may be unique to the set of input nodes selected in the instruction, and may be unknown to the user. That is, the user may be unable to use the diagnostic device to generate the expected combination code prior to receiving the instruction, and must wait to receive the instruction before being able to use the diagnostic device to generate the expected combination code. In exemplary embodiments, the instruction may be generated by a computing device or by a supervisor. In an exemplary embodiment, the instruction may be provided to the user by a computer-implemented and computer-executable method. In an exemplary embodiment, the instruction may be provided by a telephone call, a phone message, an email message, a telephone text message, and the like.

In an exemplary embodiment, the instruction may be provided a short time before, at, or a short time after a scheduled medication time. The instruction may be specific to the particular dose of the medication taken by the user, and the selection of the input nodes in the instruction may result in a particular combination code being generated in the diagnostic device.

In step 1006, the user may introduce the sample at the selected one or more input nodes in the diagnostic device. In an exemplary embodiment, a sample may be introduced to the diagnostic device as a suitable liquid sample, for example, a pure liquid, a combination or mixture of multiple liquids, a solution or mixture in a liquid (e.g., water, oil, etc.), a supernatant from a liquid suspension of solids, and the like. In an exemplary embodiment, a liquid sample may include particles, for example, nanoparticles, nanocrystals, nanomaterials, colloids and the like.

Any suitable number of samples may be introduced at any suitable number of input nodes in the diagnostic device. In an exemplary embodiment, a single sample or a combination of samples may be introduced at an input node. For example, a single blood sample may be introduced at a single input node, or a combination of two blood samples may be introduced at a single input node. In an exemplary embodiment, a sample may be introduced at more than one input node.

In step 1008, the sample introduced at an input node may flow or wick along one or more microfluidic channels to one or more corresponding output nodes in the diagnostic device. In an exemplary embodiment in which the microfluidic channels are provided in a paper-based network layer, the sample may wick through the channels by capillary action without the use of or need for an external pump mechanism. As the sample flows through a channel, the sample may interact with one or more reagents provided at the input node, at one or more locations in the channel, and/or at the output nodes. In an exemplary embodiment, the sample interacts with a first set of one or more reagents along the channels and a second set of one or more reagents at the output nodes.

In step 1010, the interaction of the sample with the one or more reagents may result in the appearance or absence of visible indicators at one or more output nodes. The combination of the visible indicators at the output nodes constitutes a combination code. In an exemplary embodiment, the combination code may be a particular sequence of numbers, a particular sequence of letters, a particular sequence of symbols, a particular sequence of numbers in a particular color sequence, a particular sequence of letters in a particular color sequence, a particular sequence of symbols in a particular color sequence, and the like. In an exemplary embodiment, the combination code appearing at the output nodes may be unique to the set of input nodes at which the sample was introduced. In this exemplary embodiment, the combination code revealed depends on the particular sequence of input nodes used in accordance with the instruction. For example, use of only input node A may reveal a code only in output node 1, use of input node C may reveal codes in output nodes 2 and 3, use of input node D may reveal a code in output node 3, and use of input node E may reveal codes in output nodes 4 and 5, use of only input node B may not reveal any code.

Use of the diagnostic device in accordance with each instruction thus results in the generation of a particular predetermined combination code at the output nodes. In an exemplary embodiment, the combination code is not known to the user but may be known to a supervisor as being associated with the selected set of input nodes or may be stored on a computing device. The use of the diagnostic device based on different instructions may thereby result in different resulting combination codes. Thus, if the user is able to transmit an expected combination code associated with the selected set of input nodes indicated in the instruction, then it may be determined that the user used the diagnostic device only after receiving the instruction. If the interaction of the sample with the reagents indicates that the user took a medication, then making the user wait for the instruction ensures that the combination code is relevant to the user's current dose of the medication and not to a previous dose of the medication.

Exemplary embodiments thereby overcome a loophole in certain conventional diagnostic systems in which a user can take a medication on the first day of a medication regimen, activate diagnostic tests for multiple days, and write down the combination codes for the following days. This loophole defeats the regular reporting mechanism that is achieved with reliability in exemplary embodiments. As such, exemplary embodiments allow remote determination of whether a user has in fact taken a dose of a medication.

In step 1012, in an exemplary embodiment, the combination code appearing at the output region of the diagnostic device may be read off manually by the user or automatically by a suitable image capture device. Exemplary image capture devices may include, but are not limited to, a barcode scanner, tablet computer (e.g., the iPad™ tablet computer), mobile computing or communication device (e.g., the iPhone™ mobile communication device, the Android™ mobile communication device, and the like), a workstation, desktop computer, server, laptop, handheld computer, or other form of image capture, computing or telecommunications device that is capable of communication and that has sufficient processor power and memory capacity for capturing an image of the combination code. In an exemplary embodiment, the user may capture an image of the combination code using a mobile camera phone.

In step 1014, in an exemplary embodiment, the image capture device may perform computational or image analysis of the captured image to interpret the combination code. Interpretation of the combination code allows the device to automatically determine whether a marker or characteristic is present or absent in the sample. Exemplary embodiments may recognize the combination code in the image, compare the imaged combination code to a stored database of predefined codes, and identify a diagnostic result corresponding to an identified code in the stored database. In an exemplary embodiment, interpretation of the combination code may also allow the device to automatically determine whether a secondary diagnostic condition exists in the sample or the user from whom the sample was derived. For example, if the combination code indicates presence of nitrites in a urine sample, the device may automatically determine that this indicates the presence of the secondary diagnostic condition of a urinary tract infection.

In some cases, the degree of interaction between the sample and the reagents in the diagnostic device may affect the intensity of the visible indicators at the output nodes. For example, a larger amount, volume, concentration or strength of a marker in the sample may result in a higher intensity of the visual indicator, and vice versa. Exemplary embodiments may detect the intensity of a visible indicator at an output node to quantitatively determine the degree or extent of a marker or characteristic in the sample. For example, a darker colored indicator at an output node corresponding to creatine may be analyzed to quantitatively determine that a high level of creatine is present in a urine sample. Conversely, a lighter colored indicator at an output node corresponding to creatine may be analyzed to quantitatively determine that a low level of creatine is present in a urine sample.

In an exemplary embodiment, the qualitative and/or quantitative determination of a marker or characteristic in a sample may be used to make a secondary determination of, for example, a diagnostic condition associated with the sample or the user from which the sample was obtained. For example, in checking urine creatine levels for a drug test, detection of a creatine level in a urine sample that is lower than a predetermined threshold may indicate that an associated drug test may have been manipulated by the user.

In an exemplary embodiment, an image capture device that captures an image of the combination code may also interpret the combination code. In another exemplary embodiment, an image capture device that captures an image of the combination code may not itself interpret the combination code, but may transmit it to another computational device or to a user for interpretation of the combination code. In this exemplary embodiment, the computational device that performs the interpretation may be provided with the image capture device, may be coupled to the image capture device, or may be provided remotely from the image capture device.

The capture and interpretation of the combination code in an exemplary diagnostic device allow for rapid point-of-care detection of markers and characteristics of interest in samples. This detection and interpretation may be accomplished in an efficient manner using exemplary diagnostic devices without the need for specialized equipment or training. This allows exemplary diagnostic devices to detect and analyze samples at a faster rate compared to conventional centralized lab assays that require special equipment, training and reagents.

In step 1016, in an exemplary embodiment, one or more results associated with the combination code may be displayed at a visual display device, for example, at the location of the user or remotely from the user (e.g., at a hospital that is remote from the diagnostic device and from the user). Exemplary displayed results may include, but are not limited to, the combination code itself, the presence or absence a marker or characteristic of the sample corresponding to the combination code, a secondary diagnostic condition associated with the sample, the source of the sample (e.g., an identification of the person from whom the sample was derived), an identification of the diagnostic device, a geographical location of the diagnostic device (e.g., using a GPS device provided in or with the diagnostic device), the date and time of use of the diagnostic device, and the like. In an exemplary embodiment, a combination code corresponding to a particular user may be associated with an identifier for the user.

In step 1018, in an exemplary embodiment, instructions may be sent to store one or more diagnostic results associated with the combination code in a central storage, for example, a central server, a central database, and the like. In an exemplary embodiment, the combination code may be transmitted by a computer-implemented and computer-executable method. In an exemplary embodiment, the combination code may be transmitted by a telephone call, a phone message, an email message, and the like.

In step 1020, in an exemplary embodiment, one or more diagnostic results associated with the combination code may be stored in the central storage. In an exemplary embodiment, the central storage may store user-specific results obtained from multiple diagnostic devices used by a single user. In another exemplary embodiment, the central storage may store distributed results obtained from multiple diagnostic devices used by multiple users. The users may be located at the same or at different geographical locations.

Multiple exemplary diagnostic devices distributed to many users enable broad and real-time surveillance of diseases and pathogens and their early detection. This allows for rapid crowdsourcing of diagnostic results that may allow epidemiological studies and detection of pathogens, disease conditions, and the like, affecting a population of people and/or a geographical location. Broad-based use of exemplary diagnostic devices may also enable early localization of infected areas via, for example, mobile phone reporting and geographic information system (GIS) mapping.

In an exemplary embodiment, broad-based use of exemplary diagnostic devices may allow aggregation of test data from multiple users to generate a profile of test data for a particular geographical location or a particular demographic characteristic. For example, a "health map" may be generated based on data received from the diagnostic devices. An exemplary "health map" is advantageous over conventional health data reports that aggregate health data received from news reports and word-of-mouth. In contrast to these conventional health data reports, an exemplary "health map" is generated based on real-time actual diagnostic results, instead of the less specific and less accurate clinical case reporting used in generating conventional health data aggregates. Exemplary "health maps" thus allow more reliable and accurate field diagnostic data collection and analysis.

Furthermore, exemplary diagnostic devices allow detection of prognostic biomarkers in a biological sample obtained from a patient that reflect disease severity. Prognosis prediction is a significant medical challenge, and military and civilian medical personnel have a pressing need to identify patients at high risk of sudden death or progression to life-threatening disease states. An exemplary diagnostic device may be used to detect one or more biomarkers associated with a high risk of sudden death or progression to very serious disease states. Detection of these biomarkers in an exemplary diagnostic device may allow real-time alerting of medical personnel as to the severity of a patient's disease or the risk of death for the patient. For example, the diagnostic device or a communication device associated with the diagnostic device may be used to transmit the alert to medical personnel upon detection of the relevant biomarkers.

Exemplary embodiments may also enable monitoring of the compliance of a user with a medication or testing regimen, e.g., whether the user is taking doses of a medication at scheduled times, whether the patient is following the correct protocol for a drug testing regimen, and the like. Exemplary embodiments are usable for monitoring and ensuring patient compliance to treatment regimens for any suitable medication including, but not limited to, medications for tuberculosis (TB), malaria, diabetes, heart disease, bacterial infections, and the like. Based on the presence or absence of one or more medical metabolites in a sample, exemplary methods may also determine that the user has taken a dose of a medication. In an exemplary embodiment, exemplary methods may provide one or more rewards to the patient for complying with the regimen. In an exemplary embodiment, exemplary methods may provide one or more penalties to the patient for failing to comply with the regimen. In an exemplary method that tests whether a patient has taken isoniazid, a TB medication, the patient's urine may be tested for isonicotinic acid which is a metabolite of the medication. The presence of isonicotinic acid in the urine confirms ingestion of the medication.

In step 1022, exemplary embodiments may determine whether the user has taken a dose of a medication based on the combination code revealed at the output region of the diagnostic device. For example, if the combination code matches a pre-determined combination code corresponding to the set of input nodes selected, then exemplary embodiments may determine that the combination code indicates that the user has taken a dose of the medication and that the result is specific to the current dose of the medication.

In step 1024, exemplary embodiments may transmit compliance information to a health center. The information may include whether the user is complying with the medication regimen, when the patient has taken his/her medications, and the like.

In step 1026, exemplary embodiments may transmit compliance information to a reward/penalty center. If it is determined that the user is in compliance with a medication regimen, exemplary embodiments may provide the user a reward. Small but immediate rewards may be effective in promoting behavior change in the user as they provide a benefit for doing something today versus tomorrow. For example, rewards may incentivize a user to comply with a medication regimen. Exemplary rewards may include, but are not limited to, free cell phone minutes, microfinance loans, and the like. On the other hand, if the user is not in compliance with the medication regimen to a sufficient degree, exemplary embodiments may impose a penalty on the user. Exemplary penalties may include, but are not limited to, reduction or cancellation of free cell phone minutes, reduction or cancellation of microfinance loans, and the like.

In an exemplary embodiment, the method 1000 illustrated in FIG. 10 may allow monitoring compliance for a single medication using a single diagnostic device. In another exemplary embodiment, the method 1000 illustrated in FIG. 10 may allow monitoring compliance for two or more medications using a single diagnostic device. For example, a first set of output nodes may be used to detect a biomarker, trace or metabolite of a first medication, while a second set of output nodes may be used to detect a biomarker, trace or metabolite of a second medication.

IV. THIRD NON-LIMITING EXEMPLARY DIAGNOSTIC DEVICE

Figure 11:
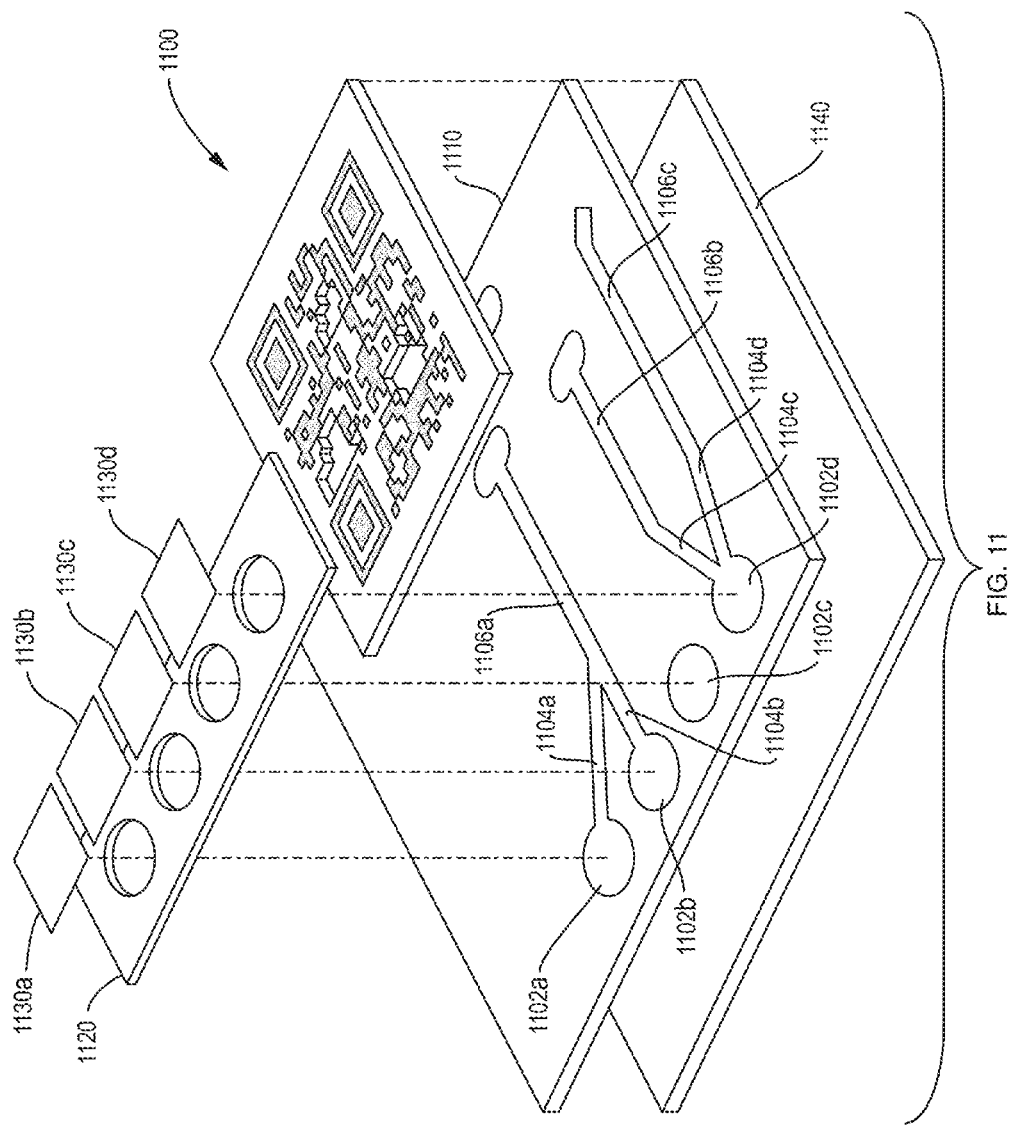
FIG. 11 illustrates an exploded perspective view of another exemplary diagnostic device showing a network of microfluidic channels.

In an exemplary embodiment, the network layer of the exemplary diagnostic device 200 illustrated in FIGS. 2A-2E may be modified to provide a plurality of input nodes mapped to a plurality of output nodes as illustrated in FIGS. 7 and 8. FIG. 11 illustrates a perspective view of an exemplary diagnostic device 1100. A bottom layer 1140 may be provided in device 1100 to support one or more layers disposed above it. An exemplary network layer 1110 may be provided above the bottom layer 1140. The network layer 1110 may include a set of one or more input nodes, a set of one or more output nodes and one or more channels connecting at least one input node to at least one output node. The channels may be substantially two-dimensional or three-dimensional. The channels may have exemplary widths ranging from about a millimeter to several millimeters.

For example, the network layer 1110 may include input nodes 1102a, 1102b, 1102c, 1102d, and output nodes 1106a, 1106b, 1106c. Input node 1102a may be in fluid communication with output node 1106a via channel 1104a. Input node 1102b may be in fluid communication with output node 1106a via channel 1104b. Input node 1102c may not be in fluid communication with any output nodes. Input node 1102d may be in fluid communication with output node 1106b via channel 1104c and with output node 1106c via channel 1104d. Similar configurations may be provided in the network layer 1110. The network layer 1110 may include reagents at the input nodes, the output nodes and/or the channels, for detecting the presence or absence of one or more markers in one or more samples. The one or more reagents may be embedded in the network layer or may coat components of the network layer.

The input nodes 1102a, 1102b, 1102c, 1102d in the network layer 1110 are configured to allow introduction of one or more samples to the diagnostic device 1100. Each input node may be identified by a visual identifier visible to the user at all times including, but not limited to, a number, a set of numbers, a letter, a set of letters, a symbol, a color, or any combination thereof. In an exemplary embodiment, each input node is identified by a unique identifier. In the exemplary embodiment illustrated in FIG. 7, the input nodes are organized linearly along a straight line. In other exemplary embodiments, the input nodes may be organized in any suitable configuration, e.g., circular arrangements, oval arrangements, wavy arrangements, rectangular arrangements, random arrangements, scattered arrangements, and the like.

The output nodes 1106a, 1106b, 1106c in the network layer 1110 are configured to display one or more visual indicators due to the interaction of markers in the samples with one or more reagents. In the exemplary embodiment illustrated in FIG. 11, the output nodes 1106a, 1106b, 1106c are organized linearly along a straight line. In other exemplary embodiments, the output nodes 1106a, 1106b, 1106c may be organized in any suitable configuration, e.g., circular arrangements, oval arrangements, wavy arrangements, rectangular arrangements, random arrangements, scattered arrangements, and the like. In an exemplary embodiment, the numbers of input nodes 1102a, 1102b, 1102c, 1102d and output nodes 1106a, 1106b, 1106c may be the same. In another exemplary embodiment, the numbers of input nodes and output nodes may be different.

In an exemplary embodiment, each output node may include a hidden indicator or code that is revealed only when the presence or absence of a marker is detected in the sample. The reaction may be a colorimetric reaction and may cause a color change at the output node that may reveal a hidden indicator. In other exemplary embodiments, other types of interactions (e.g., electrochemical interactions) may take place between the marker in the sample and the reagents. Exemplary indicators may include, but are not limited to, a number, a set of numbers, a letter, a set of letters, a symbol, a color, or any combination thereof.

A top layer 1120 may be provided to cover the network layer 1110 to prevent a user from viewing the mapping between the input nodes 1102a, 1102b, 1102c, 1102d and the output nodes 1106a, 1106b, 1106c in the network layer. In an exemplary embodiment, apertures may be provided in the top layer 1120 aligned with the input nodes 1102a, 1102b, 1102c, 1102d, respectively. In an exemplary embodiment, removable covers or tabs 1130a, 1130b, 1130c, 1130d may be used to cover the apertures before use of the device. A user may selective remove one or more covers to access corresponding input nodes. The removable covers provide a user-activated valve mechanism to select one or more input nodes 1102a, 1102b, 1102c, 1102d, and thereby the channels that are activated at any given time. This provides a switching or valving mechanism by which a user may selectively make connections in the diagnostic device.

In an exemplary embodiment, a user may punch out certain input nodes and/or channels to select activation points in an inverse fashion by blocking access to the punched-out input nodes and/or channels. One or more removable tabs may be provided in the input nodes and/or channels to enable the user to remove material from the input nodes and/or the channels. For example, removal of a tab may result in the removal of material from a corresponding input node or channel, thereby breaking the connection between the input node and an output node. This provides a switching or valving mechanism by which a user may selectively break connections in the diagnostic device.

In the exemplary device 1100, different mapping schemes may be implemented using the channels provided between the input nodes and the output nodes. In an exemplary embodiment, the channels may provide fluid communication between at least one input node and at least one output node. The mapping scheme between the input nodes and the output nodes may be random or non-random. In an exemplary embodiment, exemplary mapping schemes may include mapping of one or more input nodes, each to a single output node; mapping of one or more output nodes, each to a single input node; mapping of one or more input nodes, each to two or more output nodes; mapping of one or more output nodes, each to two or more input nodes; mapping of two or more output nodes to a single input node; mapping of two or more input nodes to a single output node; not mapping one or more input nodes to any output node; not mapping one or more output nodes to any input node; mapping a single input node to a single output node; and the like. Any combination of one or more of these mapping schemes may be present in an exemplary diagnostic device. Cross-mapping of an input node to multiple output nodes allows detection of multiple markers at the different output nodes.

One of ordinary skill in the art will recognize that the mapping between input and output nodes shown in FIG. 11 is merely illustrative and that any suitable mapping scheme may be implemented in exemplary embodiments.

In an exemplary embodiment, a complex mapping scheme is provided between the input nodes and the output nodes that is non-obvious to a user and is hidden from the view of the user by the top layer 1120. This prevents the user from guessing which indicators may be revealed from introduction of the sample to a selected set of input nodes. The mapping of the input nodes to the output nodes may be known to a supervising entity that monitors a user's compliance with a medication regimen. Thus, the supervising entity knows the indicators at output nodes associated with a particular set of input nodes, but the user may not know the combination of indicators associated with a set of input nodes prior to the indicators being revealed at the output nodes. Thus, the hidden mapping between the input nodes and output nodes provides encryption of the diagnostic mechanism to the user of the device, such that the user cannot predict which combination of indicators will be revealed in response to introduction of the sample at a particular set of input nodes.

An exemplary diagnostic device may include one or more die markers at the input nodes, the output nodes and/or the channels. A sample taking two different channels between input and output nodes may result in differently colored indicators at the output nodes if the channels contain different die markers. The placement of the die markers may be hidden from the user and, as such, the colors that appear at the output nodes may also be used as part of the combination of indicators. In an exemplary embodiment, introduction of a sample at a particular set of input nodes may reveal a combination of indicators consisting of a set of codes and colors at one or more output nodes. For example, in the exemplary embodiment of FIG. 11, a sample introduced at input node 1102a may pick up a first die marker in channel 1104b to result in a purple-colored indicator at output node 1106a, while a sample introduced at input node 1102d may pick up a different second die marker in channel 1104d to result in a blue-colored indicator at output node 1106c.

In an exemplary embodiment, the indicator appearing at an output node may depend on other variables including, but not limited to, the type of the sample used (e.g., saliva, urine, sweat, blood, blister exudate, and the like), the type of marker that interacts with the reagents in the device (e.g., sugar, medication, hormone, and the like).

In an exemplary embodiment in which the diagnostic device is used to detect the presence or absence of a marker in a sample, one or more output nodes may include indicators that are revealed when the marker, if present in the sample, interacts with the reagents in the device. In another exemplary embodiment in which the diagnostic device is used to detect the presence or absence of two or more markers in a sample, different sets of output nodes may include indicators that are revealed when the different markers, if present in the sample, interact with the reagents in the device. For example, a first set of output nodes (e.g., output node 1106a) may include indicators that are revealed when a drug metabolite is present in a patient's urine, and a second set of output nodes (e.g., output nodes 1106b, 1106c) may include indicators that are revealed when a sugar is present in a patient's urine.

In an exemplary embodiment, a sample (e.g., the patient's blood, blister exudate, saliva, urine, sweat, and the like) may be used to determine whether a patient has a secondary condition (e.g., whether the patient has taken a particular medication, whether the patient has a particular physical condition like a disease, and the like). The one or more reagents present in an exemplary diagnostic device may react with one or more markers in the sample to indicate whether the patient has the secondary condition. In an exemplary embodiment, the condition may be diagnosed based on the presence or absence of a single marker in the sample. In another exemplary embodiment, the condition may be diagnosed based on the presence or absence of two or more markers in the sample. In another exemplary embodiment, one or more sample may be tested to determine whether a patient has two or more conditions (e.g., whether the patient has multiple diseases, whether the patient has a disease and whether the patient has taken a medication, whether the patient has taken two medications, whether the patient is intoxicated and has taken a medication).

Components of the exemplary diagnostic device 1100 of FIG. 11 similar or common to the exemplary diagnostic device 200 of FIGS. 2A-2E are described in connection with FIGS. 2A-2E.

V. EXEMPLARY MARKERS AND CHARACTERISTICS OF SAMPLES

Exemplary diagnostic devices may be used to detect the presence or absence of one or more markers or characteristics in one or more samples. Detection of a marker in a sample may indicate that the sample has a corresponding biological state. Exemplary biological states may include, but are not limited to, normal biological states (e.g., certain concentrations of sugar in a blood sample), pathogenic states (e.g., a virus in a tissue sample, a bacterium in a soil sample), pharmacologic states or responses (e.g., drug metabolites in a blood sample), and the like. Certain exemplary markers may include, but are not limited to, proteins, nucleic acids, sugars, food, water, soil components, drugs, drug metabolites, biomarkers, tracers, biological organisms like viruses, bacteria, one or more environmental factors (e.g., pH), one or more controlled substances (e.g., narcotics), one or more chemical compounds (e.g., oils, fuels, chemical additives), and the like.

In certain embodiments, the marker may be a nucleic acid. A nucleic acid may be any suitable form of single- or double-stranded nucleic acid, such as, but not limited to, a single stranded RNA, double stranded RNA, DNA, or aptamers. In other certain embodiments, the marker may be a protein. Where the marker is a protein, the marker may be any suitable form of protein, such as, but not limited to, an antigen, antibody or fragment thereof, structural protein, or epitope.

Exemplary diagnostic devices may be used to simultaneously detect a nucleic acid and a protein in a sample. For example, exemplary diagnostic devices may be used to detect the presence of a lipid in a biological sample, for example, cholesterol or triglyceride.

In other exemplary embodiments, the diagnostic devices may be used to detect the presence or absence of an enzyme or glucose in a sample.

In other exemplary embodiments, the one or more markers or characteristics may include nucleic acids or polypeptide markers associated with a pathological condition or disease. In another exemplary embodiment, the one or more markers or characteristics may include nucleic acids or polypeptides associated with a nutritional state or condition.

In yet other exemplary embodiments, the one or more markers or characteristics may include cell markers associated with cell cycle and growth. In another exemplary embodiment, the one or more markers or characteristics are associated with cell proliferation and differentiation. In one embodiment, cell markers are associated with cancer. In one embodiment, the different markers or characteristics detected are infectious agents. In certain examples, the infectious agent may be derived from a virus, a bacterium, a parasite, and the like. Accordingly, in certain embodiments, viruses or components of viruses (e.g., polypeptides) may be derived from, but are not limited to, a virus such as an influenza virus, HIV, hepatitis virus, adenovirus, enterovirus, parainfluenza virus, or the like. For example, the infectious agent may be a bacterium such as *Streptococcus pneumoniae, Staphylococcus aureus, Bordetella pertussis, Mycoplasma pneumoniae* or a fungus such as yeast.

Exemplary diagnostic devices may also be used to detect the presence of drugs or other agents present in a biological sample. For example, the test devices may be used to screen for the presence of certain drugs, such as, but not limited to, marijuana, cocaine, amphetamine, methamphetamine, opiates, barbiturates, alcohol, and the like.

Exemplary diagnostic devices may also be used to detect the presence of one or more chemical compounds including, but not limited to, oils, fuels, chemical additives, and the like. In one example, a sample of a fuel may be tested using an exemplary diagnostic device to detect the presence or absence of one or more constituent compounds. This may enable determination of whether the right type of fuel is being used. This may also enable detection of an illegal additive in the fuel. This may also enable checking the health of the vehicle from which the fuel sample was derived.

Certain exemplary diagnostic devices may enable multi-step tests or diagnostics. In detecting a marker or in determining whether a user has taken a medication, the results of the detection may be thrown off or corrupted by certain other markers in the sample. For example, a high blood sugar may cause a false positive in the detection of a medication metabolite or in the detection of a strep throat virus in a sample. Exemplary diagnostic devices may enable a first test for a marker (e.g., a medication metabolite or a strep throat virus), and a subsequent follow-up test for the marker to ensure a more robust test result and to ensure that the first test did not result in a false positive.

In an exemplary method of performing a multi-step test or diagnosis, a user may select one or more input nodes and remove tabs covering the input nodes. The user may introduce one or more samples at the selected input nodes. In an example, the sample may result in the appearance of indicators at output nodes C and D in the diagnostic device, a combination of indicators that indicates that the sample contains a metabolite of a medication. This indicates that the user has taken a medication. The diagnostic device may also show an indicator at output node E which indicates a high blood sugar. Since high blood sugar can sometimes cause a false positive at output nodes C and D in the diagnostic device, the user may perform a follow-up test to ensure that the sample does indeed contain the medication metabolite. The user may, for example, perform the same test for the medication metabolite or a different test for the medication metabolite using the same or a different diagnostic device. The user may alternatively observe another output node F in the diagnostic device that may present a more robust indicator for the presence of the medication metabolite. That is, the medication metabolite may interact with a first set of reagents in order to present an indicator at output nodes C and D, and may interact with a second set of reagents in order to present an indicator at output node F. In an example, the interaction of the medication metabolite with the second set of reagents may be a slower reaction than the interaction of the medication metabolite with the first set of reagents. If output node F also shows an indicator, the user may be assured that the result at output nodes C and D was not a false positive. On the other hand, if output node F does not show an indicator, this may indicate that the result at output nodes C and D was a false positive.

VI. EXEMPLARY USE OF GOLD NANOPARTICLES TO DETECT AN ANTIBODY

One of ordinary skill in the art will recognize that any suitable set of one or more reagents may be used to interact with a marker or characteristic in a sample. An exemplary reagent usable in an exemplary diagnostic device is gold nanoparticles which exhibits a red color when an antibody binds to it. The gold nanoparticles may have an exemplary diameter of about 8.5 nm. The gold nanoparticles may be provided in an exemplary diagnostic device so that an antibody in a sample may bind to the gold nanoparticles. In the presence of sodium chloride (NaCl) and an antibody, the aggregation state of the gold nanoparticles may depend on the concentration of the antibody. The aggregation state of the gold nanoparticles may, in turn, affect the color of the gold nanoparticles visible to a user. For example, when a low concentration of the antibody is present, the gold nanoparticles aggregate and turn blue. On the other hand, when the concentration of the antibody is above a threshold of about 50 µg/mL, the gold nanoparticles remain unaggregated, bind to the antibody, and turn pink. The pink color of the gold nanoparticle thereby indicates that a certain minimum concentration of the antibody is present in a sample.

Figure 14A:
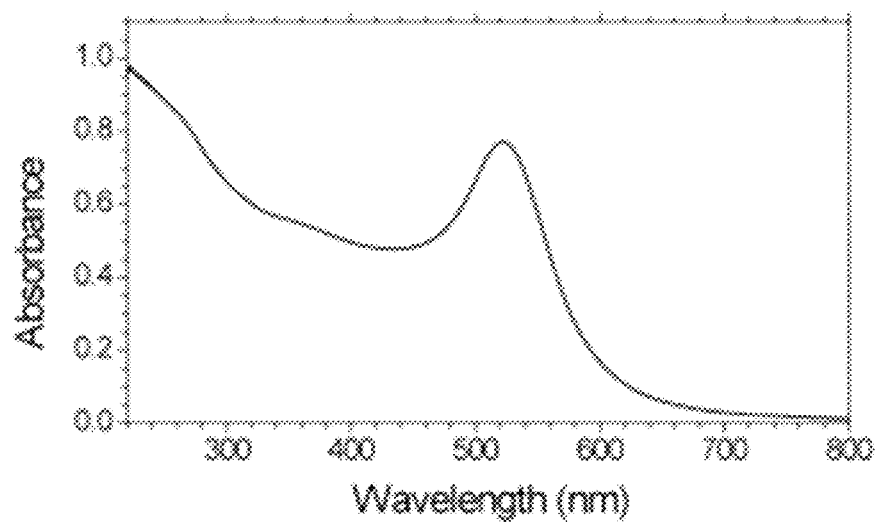
FIG. 14A is a graph of the wavelength of maximum optical absorption of gold nanoparticles (in nanometers along the y-axis) against different concentrations of an antibody (in mg/mL along the x-axis).

FIG. 14A is a graph of the wavelength of maximum optical absorption of gold nanoparticles (in nanometers along the y-axis) against different concentrations of an antibody (in mg/mL along the x-axis). The color change of the gold nanoparticles may be monitored by the wavelength of maximum absorption that shifts from about 620 nm to about 520 nm when a sufficient concentration of the antibody is bound to the gold nanoparticles.

Figure 14B:
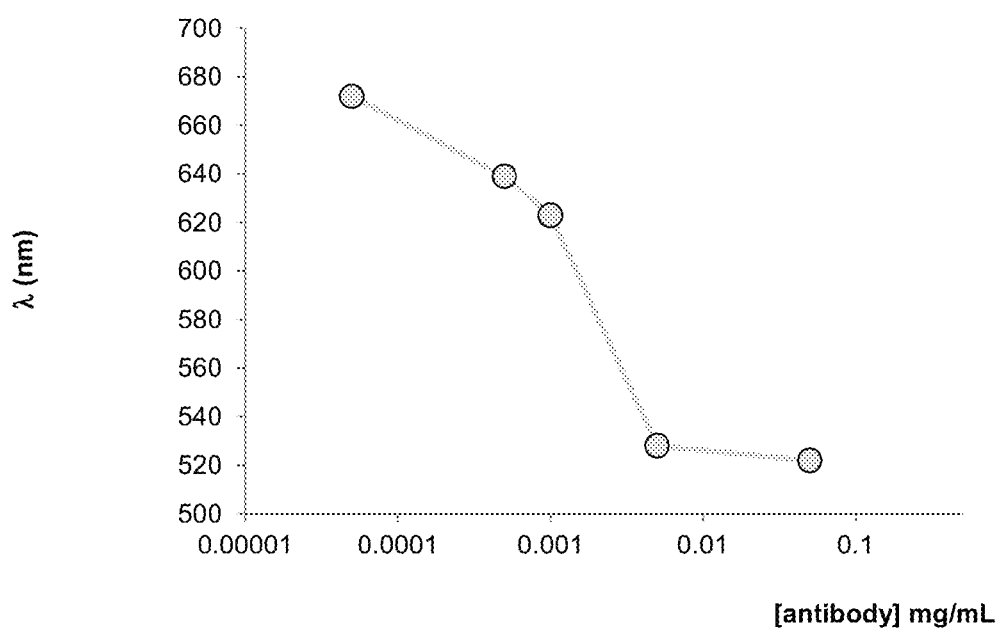
FIG. 14B is a graph of the optical absorption of gold nanoparticles (in fractions of one along the y-axis) against different wavelengths (in nm along the x-axis).

FIG. 14B is a graph of the optical absorption of gold nanoparticles (in fractions of one along the y-axis) against different wavelengths (in nm along the x-axis), showing an absorption maximum at about 520 nm which results in a strong red or pink color.

VII. IMPLEMENTATION OF PATTERN DETECTION IN EXEMPLARY EMBODIMENTS

Any suitable technique may be used to detect or capture an image of a visible pattern or code appearing at the output region of an exemplary diagnostic device, transmit the image, and interpret the pattern or code to determine a diagnostic result associated with a sample. An exemplary diagnostic device may include or be connectable to a communication or computing device that automatically detects a two-dimensional pattern or code revealed at an output region of the device. The computing device may implement any suitable technologies for automatically detecting the pattern or code revealed at the output region of an exemplary diagnostic device. In an exemplary embodiment, an image capture device, e.g., camera, a phone equipped with a camera, a computer equipped with a webcam, may be used to capture an image of the pattern or code. Computer-implemented optical character recognition (OCR) techniques may be used to read the pattern or code from the image. In another exemplary embodiment, a barcode reading device or a card-reading device may be used to read the pattern or code directly from the output region of the device.

In an exemplary embodiment, the device may automatically transmit an image of a two-dimensional pattern or code to another entity, e.g., a database, a storage device, a distributed storage, cloud storage, another computing device, a human user, a compliance monitoring center or device, and the like.

In an exemplary embodiment, an image of the two-dimensional pattern or code may be interpreted automatically by a computing device. For example, if a particular pattern or code is associated with a particular condition in a patient (e.g., a particular disease), the computing device may determine that the condition exists and may communicate this information to the patient and/or the compliance monitoring center or device.

In an exemplary embodiment, information may be provided to the patient and/or the compliance monitoring center or device to facilitate in interpreting the pattern or code. The information may be used to determine whether a particular condition exists in the patient (e.g., a particular disease) based on the pattern or code generated at the output region. For example, the information may indicate that a particular pattern or code corresponds to a particular condition. The information may be provided in any suitable way including, but not limited to, verbally, in writing, in the form of a chart, on a visual display device connected to a computing or storage device, and the like. An exemplary computing device is illustrated in and described with reference to FIG. 12.

VIII. IMPLEMENTATION OF RFID TRANSMISSION IN EXEMPLARY EMBODIMENTS

In an exemplary embodiment, one or more radio frequency identification (RFID) tags may be associated with an output region of an exemplary diagnostic device. In an exemplary embodiment, upon revelation of a particular machine-readable pattern or code at the output region or upon detecting a particular interaction of a sample, the RFID tag may transmit the pattern or code encoded in a radio frequency (RF) signal. The RFID tag may also transmit other information regarding the use of the diagnostic device, for example, an identification of the diagnostic device, an identification of the user of the diagnostic device, the date and time, and the like.

One or more RFID antennae may be provided in the vicinity of the diagnostic device or remotely from the diagnostic device to detect the transmitted RF signal and the encoded pattern or code. In an exemplary embodiment, the RF antenna may be provided at a compliance monitoring center or device in order to monitor whether the correct pattern or code has been generated. In another exemplary embodiment, the RF antenna may be located at a different location than the compliance monitoring center or device, and may detect and forward information contained in the RF signal to the compliance monitoring center or device.

One of ordinary skill in the art will recognize that any suitable technology may be used to automatically transmit or re-transmit a pattern or code detected at the output region of an exemplary diagnostic device.

IX. EXEMPLARY COMPUTING DEVICES AND NETWORK ENVIRONMENTS

Figure 12:
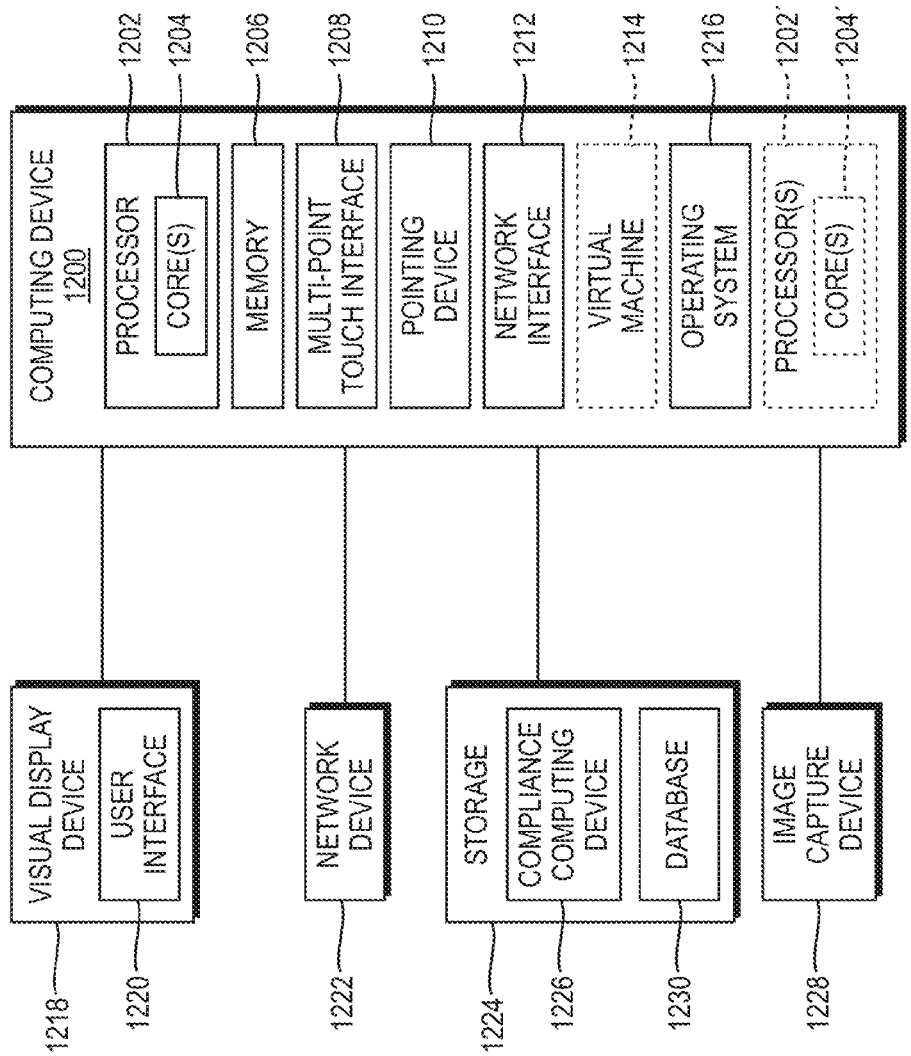
FIG. 12 illustrates a block diagram of an exemplary computing device that may be used to perform the methods provided by exemplary embodiments.

FIG. 12 illustrates a block diagram of an exemplary computing device 1200 that may be used to perform any of the methods provided by exemplary embodiments. Exemplary computing device 1200 may be any computer system, such as a workstation, desktop computer, server, laptop, handheld computer or other form of computing or telecommunications device that is capable of communication and that has sufficient processor power and memory capacity to perform the operations described herein.

The computing device 1200 may include one or more non-transitory computer-readable media for storing one or more computer-executable instructions or software for implementing exemplary embodiments. The computer-readable media may include, but are not limited to, one or more types of hardware memory, non-transitory tangible media, and the like. For example, memory 1206 included in the computing device 1200 may store computer-executable instructions or software for implementing exemplary embodiments. The computing device 1200 may include processor 1202 and one or more processor(s) 1202' for executing computer-executable instructions or software stored in the memory 1206, and other programs for controlling system hardware. Processor 1202 and processor(s) 1202' may each be a single core processor or multiple core (1204 and 1204') processor.

Virtualization may be employed in the computing device 1200 so that infrastructure and resources in the computing device may be shared dynamically. A virtual machine 1214 may be provided to handle a process running on multiple processors so that the process appears to be using only one computing resource rather than multiple computing resources. Multiple virtual machines may also be used with one processor.

Memory 1206 may include a computer system memory or random access memory, such as DRAM, SRAM, EDO RAM, and the like. Memory 1206 may include other types of memory as well, or combinations thereof.

A user may interact with the computing device 1200 through a visual display device 1218, such as a computer monitor, which may display one or more user interfaces 1220 or any other interface. The visual display device 1218 may also display other aspects, elements and/or information or data associated with exemplary embodiments. The computing device 1200 may include other I/O devices such a keyboard or a multi-point touch interface 1208 and a pointing device 1210, for example a mouse, for receiving input from a user. The keyboard 1208 and the pointing device 1210 may be connected to the visual display device 1218. The computing device 1200 may include other suitable conventional I/O peripherals.

The computing device 1200 may include a storage device 1224, such as a hard-drive, CD-ROM, or other computer readable media, for storing data and computer-readable instructions or software that implement exemplary embodiments. The storage device 1224 is connectable to the computing device 1200 and may transmit to and receive from the computing device 1200 data, information and/or instructions. In an exemplary embodiment, the storage device 1224 may include a compliance computing device 1226 that monitors and determines a user's compliance with a medication regimen.

In an exemplary embodiment, the storage device 1224 may also include a database 1230 for storing one or more machine-readable patterns generated by one or more diagnostic devices and any associated data, for example, an identifier for a source of a sample. In an exemplary embodiment, the database 1230 may store mappings between different machine-readable patterns and the markers/analytes/characteristics/conditions to which the patterns correspond.

The computing device 1200 may include or may be connectable to an image capture device 1228, e.g., a camera, that may be used to detect a machine-readable pattern or code revealed at the output region or output nodes of an exemplary diagnostic device.

The computing device 1200 may include a network interface 1212 configured to interface via one or more network devices 1222 with one or more networks, e.g., Local Area Network (LAN), Wide Area Network (WAN) or the Internet through a variety of connections including, but not limited to, standard telephone lines, LAN or WAN links (e.g., 802.11, T1, T3, 56 kb, X.25), broadband connections (e.g., ISDN, Frame Relay, ATM), wireless connections, controller area network (CAN), or some combination of any or all of the above. The network interface 1212 may include a built-in network adapter, network interface card, PCMCIA network card, card bus network adapter, wireless network adapter, USB network adapter, modem or any other device suitable for interfacing the computing device 1200 to any type of network capable of communication and performing the operations described herein.

The computing device 1200 may run any operating system 1216, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. The operating system 1216 may be run in native mode or emulated mode.

Figure 13:
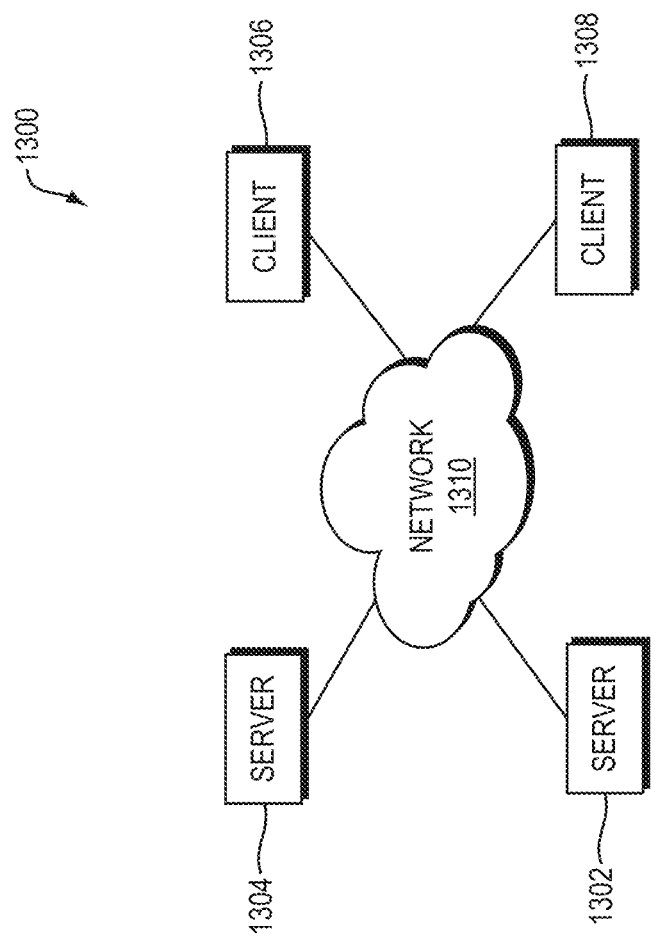
FIG. 13 is an exemplary network environment suitable for a distributed implementation of exemplary embodiments.

FIG. 13 is an exemplary network environment 1300 suitable for a distributed implementation of exemplary embodiments. The network environment 1300 may include one or more servers 1302 and 1304 coupled to one or more clients 1306 and 1308 via a communication network 1310. The network interface 1212 and the network device 1222 of the computing device 1200 enable the servers 1302 and 1304 to communicate with the clients 1306 and 1308 via the communication network 1310. The communication network 1310 may include, but is not limited to, the Internet, an intranet, a LAN (Local Area Network), a WAN (Wide Area Network), a MAN (Metropolitan Area Network), a wireless network, an optical network, and the like. The communication facilities provided by the communication network 1310 are capable of supporting distributed implementations of exemplary embodiments.

In an exemplary embodiment, the servers 1302 and 1304 may provide the clients 1306 and 1308 with computer-readable and/or computer-executable components or products under a particular condition, such as a license agreement. The computer-readable and/or computer-executable components or products may include one or more machine-readable patterns generated by a diagnostic device.

Alternatively, in another exemplary embodiment, the clients 1306 and 1308 may provide the servers 1302 and 1304 with computer-readable and/or computer-executable components or products under a particular condition, such as a license agreement. The computer-readable and/or computer-executable components or products may include one or more machine-readable patterns generated by a diagnostic device.

X. INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and may be used in conjunction with or substituted for components and methods described elsewhere in the disclosure within the scope of the invention.

XI. EQUIVALENTS

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by $\frac{1}{20}$th, $\frac{1}{10}$th, $\frac{1}{5}$th, $\frac{1}{3}$rd, $\frac{1}{2}$, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

What is claimed is:

1. A diagnostic device for detecting a presence or absence of one or more substances in one or more samples, the diagnostic device comprising:
   a microfluidic network layer, including:
   a first set of input nodes for introduction of the one or more samples to the diagnostic device;
   an output region, including
   a first set of output nodes arranged to detect the presence or absence of a first substance in the one or more samples,
   a second set of output nodes arranged to detect the presence or absence of a second substance in the one or more samples, and
   a two-dimensional machine-readable pattern with one or more apertures and one or more solid portions overlaid over the first set of output nodes and the second set of output nodes to provide a machine-readable output indicating the presence or absence of the first substance and/or the second substance in the one or more samples; and a plurality of microfluidic channels extending between the first set of input nodes and the first and second sets of output nodes.

2. The diagnostic device of claim 1, wherein an indicator appearing at the first set of output nodes within the machine-readable output indicates the presence of the first substance in the one or more samples.

3. The diagnostic device of claim 1, wherein an indicator appearing at the second set of output nodes within the machine-readable output indicates the presence of the second substance in the one or more samples.

4. The diagnostic device of claim 1, wherein a first indicator appearing at the first set of output nodes and a second indicator appearing at the second set of output nodes within the machine-readable output indicates the presence of the first and second substances in the one or more samples.

5. The diagnostic device of claim 1, wherein the first set of output nodes is arranged to detect the presence or absence of the first substance in a first sample, and wherein the second set of output nodes is arranged to detect the presence or absence of the second substance in a second, different sample.

6. The diagnostic device of claim 1, wherein the machine-readable output is a matrix pattern.

7. The diagnostic device of claim 1, wherein the two-dimensional machine-readable pattern is imprinted on a stencil, and wherein the stencil comprises a set of the apertures aligned with the first and second sets of output nodes to enable viewing of the first and second sets of output nodes.

8. The diagnostic device of claim 1, wherein the first set of output nodes include a first reagent, and wherein interaction of a sample with the first reagent causes the presence or absence of a first indicator at the first set of output nodes.

9. The diagnostic device of claim 1, wherein one or more microfluidic channels include a first reagent, and wherein interaction of a sample with the first reagent causes the presence or absence of a first indicator at the first set of output nodes.

10. The diagnostic device of claim 1, further comprising:
an image capture device for detecting the machine-readable output at the output region.

11. The diagnostic device of claim 1, further comprising:
a computational device programmed to automatically determine the presence or absence of the first substance in the one or more samples based on the machine-readable output including or excluding a first indicator at the first set of output nodes.

12. The diagnostic device of claim 11, wherein the computational device is further programmed to automatically determine that the one or more samples includes the first substance if the machine-readable output includes the first indicator at the first set of output nodes.

13. The diagnostic device of claim 11, wherein the computational device is further programmed to automatically determine a quantitative determination of the first substance in the one or more samples.

14. The diagnostic device of claim 11, wherein the computational device is further programmed to automatically determine that the one or more samples exclude the first substance if the machine-readable output does not include the first indicator at the first set of output nodes.

15. The diagnostic device of claim 11, wherein the computational device is further programmed to automatically determine a diagnostic condition based on the machine-readable output including or excluding the first indicator at the first set of output nodes.

16. The diagnostic device of claim 1, wherein the one or more samples is blood, blister exudate, urine, sweat, saliva, food, water, a soil component, oil, or fuel.

17. The diagnostic device of claim 1, wherein the first substance is a biomarker, tracer, metabolite, protein, nucleic acid, biological organism, pathogen, oil, fuel, or chemical additive.

18. The diagnostic device of claim 1, wherein the machine-readable output includes one or more colors appearing at the first set of output nodes.

19. The diagnostic device of claim 1, wherein the machine-readable output includes one or more alphanumeric symbols appearing at the first set of output nodes.

20. The diagnostic device of claim 1, wherein the machine-readable output includes one or more pictorial symbols appearing at the first set of output nodes.

21. The diagnostic device of claim 1, further comprising:
an electrochemical reader for detecting electrochemical activity at the first set of output nodes and/or the second set of output nodes, electrochemical activity at the first set of output nodes indicating the presence or absence of the first substance in the one or more samples, electrochemical activity at the second set of output nodes indicating the presence or absence of the second substance in the one or more samples.

22. The diagnostic device of claim 1, further comprising:
a top layer disposed above the microfluidic network layer for covering the plurality of microfluidic channels from view of a user.

23. The diagnostic device of claim 1, wherein the first and second sets of output nodes are provided in a scattered arrangement within the scope of the two-dimensional machine-readable pattern.

24. The diagnostic device of claim 1, wherein the first and second sets of output nodes are provided in a matrix arrangement within the scope of the two-dimensional machine-readable pattern.

25. The diagnostic device of claim 1, wherein a first input node is coupled to two or more output nodes.

26. The diagnostic device of claim 1, wherein a first output node is coupled to two or more input nodes.

27. The diagnostic device of claim 1, wherein a first input node is not coupled to any output node.

28. The diagnostic device of claim 1, wherein a first output node is not coupled to any input node.

29. The diagnostic device of claim 1, wherein the number of input nodes is the same as the number of output nodes in the microfluidic network layer.

30. The diagnostic device of claim 1, wherein the number of input nodes is different from the number of output nodes in the microfluidic network layer.

31. The diagnostic device of claim 1, further comprising:
a radio frequency identification (RFID) tag associated with the first and second sets of output nodes in the microfluidic network layer, the RFID tag configured to transmit a radio frequency (RF) signal in response to detection of the machine-readable output.

32. A method for forming a diagnostic device for detecting a presence or absence of one or more substances in one or more samples, the method comprising:
providing a microfluidic network layer;
forming a set of input nodes in the microfluidic network layer;

forming an output region, comprising:
- a first set of output nodes arranged to detect the presence or absence of a first substance in the one or more samples,
- a second set of output nodes arranged to detect the presence or absence of a second substance in the one or more samples, and
- a two-dimensional machine-readable pattern with one or more apertures and one or more solid portions overlaid over the first set of output nodes and the second set of output nodes to provide a machine-readable output indicating the presence or absence of the first substance and/or second substance in the one or more samples; and forming a plurality of microfluidic channels extending between the first set of input nodes and the first and second sets of output nodes.

\* \* \* \* \*